United States Patent [19]

Junge et al.

[11] Patent Number: 4,585,772

[45] Date of Patent: Apr. 29, 1986

[54] AGENTS FOR COMBATING CIRCULATORY ILLNESSES AND THEIR USE

[75] Inventors: Bodo Junge; Siegfried Goldmann; Günter Thomas, all of Wuppertal; Bernward Garthoff, Hilden, all of Fed. Rep. of Germany

[73] Assignee: Bayer Aktiengesellschaft, Leverkusen, Fed. Rep. of Germany

[21] Appl. No.: 512,582

[22] Filed: Jul. 11, 1983

Related U.S. Application Data

[63] Continuation of Ser. No. 322,610, Nov. 18, 1981, abandoned.

[30] Foreign Application Priority Data

Dec. 9, 1980 [DE] Fed. Rep. of Germany ....... 3046366

[51] Int. Cl.$^4$ ................ A61K 31/505; A61K 31/535; C07D 487/04
[52] U.S. Cl. .................................... 514/229; 514/234; 514/236; 514/239; 514/267; 544/115; 544/250; 544/251; 544/91; 544/94; 548/353
[58] Field of Search ................ 544/250, 115; 424/251, 424/248.5, 248.54; 514/267, 229, 236, 234, 239

[56] References Cited

U.S. PATENT DOCUMENTS

| 3,329,679 | 7/1967 | Sulkowski et al. | 544/250 |
|---|---|---|---|
| 3,594,379 | 7/1971 | Hardtmann et al. | 544/250 |
| 3,891,638 | 6/1975 | Inaba et al. | 544/250 X |
| 4,377,580 | 3/1983 | Ueda et al. | 424/251 |

OTHER PUBLICATIONS

Hardtmann, et al., J. Org. Chem., 39(24), pp. 3599–3600 (1974).
Hardtmann, et al., J. Med. Chem., 18(5), pp. 447–453 (1975).
Grout, et al., J. Chem. Soc., 1960, pp. 3551–3557 (1960).
Leistner, et al., Z. Chem., 12, 289 (1972).
Wagner, et al., Pharmazie, 34, 209 (1979).

*Primary Examiner*—Mark L. Berch
*Assistant Examiner*—Diana G. Rivers
*Attorney, Agent, or Firm*—Sprung Horn Kramer & Woods

[57] ABSTRACT

The invention relates to pharmaceutical compositions containing active ingredients of Formula (I) and methods for the use of said compositions to treat cardiac insufficiencies. Also included in the invention are methods of the manufacture of said active ingredients of Formula (I). The invention includes, additionally, compounds of Formula (I).

21 Claims, No Drawings

AGENTS FOR COMBATING CIRCULATORY ILLNESSES AND THEIR USE

This application is a continuation of application Ser. No. 322,610, filed Nov. 18, 1981, now abandoned.

The present invention relates to the use as agents for combating circulatory illness of certain tricyclic cytosine derivatives, some of which are known. The invention further relates to certain new compounds from this class of substance and to processes for their production.

Some of the tricyclic cytosine derivatives have already been disclosed (see R. J. Grout et al, J. Chem. Soc. 1960, 3551; S. Leistner et al, Z. Chem. 12, 289 (1972); G. E. Hardtmann et al, J. Org. Chem. 39, 3599 (1974); G. Wagner and others, Pharmazie 34, 209 (1979), and G. E. Hardtmann and others, J. Med. Chem. 18, 447 (1975)); no therapeutic activity has hitherto been disclosed for any of these compounds.

Biological actions are already known for similar nitrogen-containing tricyclic compounds which clearly differ chemically from the compounds according to the invention. U.S. Pat. No. 3,329,679, for example, an action on the central nervous system is described for such similar compounds.

According to the present invention there are provided pharmaceutical compositions containing as an active ingredient a compound which is a tricyclic cytosine derivative of the formula (I)

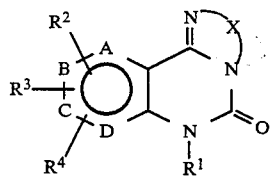

in which

X represents a bridge member having 2 or 3 carbon atoms, which is optionally substituted by 1 or 2 alkyl, aryl or aralkyl radicals, A, B, C and D each represent CH, 1 or 2 of these CH groups optionally being replaced by N in any position, $R^1$ represents a hydrogen atom or an optionally substituted straight-chain, branched or cyclic, saturated or unsaturated aliphatic hydrocarbon radical or an aryl radical, and $R^2$, $R^3$ and $R^4$ are identical or different, and each represent a hydrogen atom, an alkyl, aryl, aralkyl, alkenyl, alkoxy, aryloxy, alkylthio, arylthio, alkylsulphonyl, arylsulphonyl, alkylcarbonyl or arylcarbonyl radical, a halogen atom or a nitro, cyano, mercapto, hydroxyl, acyloxy, amino, alkylamino, acylamino, sulphonylamino, carboxyl, carboalkoxy, carboxamido, sulphonyl, aminosulphonyl or aldehyde radical, the alkyl, aryl, aralkyl, alkoxy, and aryloxy radicals mentioned being optionally substituted, in admixture with an inert pharmaceutical carrier, e.g. a solid or liquid gaseous diluent, or in admixture with a liquid diluent other than a solvent, of a molecular weight less than 200 except in the presence of a surface active agent.

The compounds used in the invention include pharmaceutically acceptable acid addition salts and bioprecursors thereof. A resulting basic compound can be converted into a corresponding acid addition salt, for example by reacting it with an inorganic or organic acid, such as therapeutically useful acid, or with a corresponding anion exchange preparation, and isolating the desired salt. An acid addition salt may be converted into the free compound by treatment with a base, e.g. a metal hydroxide, ammonia or a hydroxyl ion exchange preparation. Therapeutically useful acids are, for example, inorganic acids, e.g. hydrochloric, hydrobromic, sulfuric, phosphoric, nitric or perchloric acid, or organic acids, e.g. carboxylic or sulfonic acids, such as formic, acetic, propionic, succinic, glycollic, lactic, malic, tartaric, citric, ascorbic, maleic, hydroxymaleic, pyroracemic, phenylacetic, benzoic, 4-aminobenzoic, anthranilic, 4-hydroxybenzoic, salicyclic, aminosalicyclic, embonic, nicotinic, methanesulfonic, ethanesulfonic, hydroxy-ethanesulfonic, ethylenesulfonic, benzenesulfonic, halogenobenzensulfonic, toluensulfonic, naphthalenesulfonic and sulfanilic acid; methionine, tryptophan, lysine and arginine.

Salts of the above-mentioned acids or other salts, for example, the picrates, can also be used for purification of the bases obtained; the bases are converted into salts, the salts are separated and the bases are liberated from the salts. In view of the close relationship between the free compounds and the compounds in the form of their salts, whenever a compound is referred to in this context, a corresponding salt is also intended, provided such is possible or appropriate under the circumstances.

The compositions of the present invention have particular use in combating circulatory illnesses.

For the purposes of this specification the term 'pharmaceutically acceptable bioprecursor' of an active compound of the invention means a compound having a structural formula different from the active compounds but which nonetheless, upon administration to a warm-blooded animal is converted in the patient's body to the active compound.

According to the present invention there is further provided a process for the preparation of an active compound of the present invention, characterised in that an anthranilic acid of the formula (II)

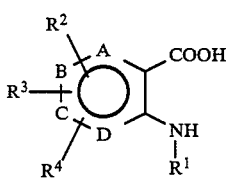

in which $R^1$, $R^2$, $R^3$, $R^4$, A, B, C and D have the meaning given above, is reacted with a chloro-carbonic acid ester of the formula $$ClCOO-R^5 \qquad (III)$$

in which $R^5$ represents an optionally substituted alkyl, aryl or aralkyl radical, in the presence of an inert aprotic solvent and with the addition of an acid-binding agent, at a temperature between −20° and 150° C., preferably between 0° and 80° C., and, after removal of the solvent, the resulting reaction product is then reacted with an excess of a diamine of the formula $$H_2N-X-NH_2 \qquad (IV)$$

in which

X has the meaning given above,
if appropriate in the presence of an inert aprotic solvent, at a temperature between 20° and 150° C., and then, after removal of excess diamine of the formula (IV) and solvent, the residue is subjected to a cyclisation at a temperature between 150° and 250° C. in an inert high-boiling solvent,
and if the product is a compound of the formula (I) in which $R^1$ denotes hydrogen and a compound of formula (I) in which $R^1$ is other than hydrogen is required, the product is treated in a subsequent reaction step with an agent of the formula $$R^1-Z \qquad (V)$$

in which $R^1$ has the meaning given above with the exception of hydrogen, and

Z represents a leaving group, such as chlorine, bromine, iodine or sulphonyl,
if appropriate under phase transfer conditions, and if a compound is obtained in which one or more of $R^2$, $R^3$ and $R^4$ are hydrogen atoms and a compound is required in which that radical or those radicals have any of the other meanings for $R^2$, $R^3$ and $R^4$, additional substituent(s) are introduced by means of a subsequent electrophilic substitution
and, if desired, the product is converted into a pharmaceutically acceptable salt thereof or into a pharmaceutically acceptable bioprecursor thereof.

Preferred active compounds of the present invention are those in which

X represents a bridge member having 2 or 3 carbon atoms, which is optionally substituted by 1 or 2 radicals selected from alkyl having 1 to 4 carbon atoms, phenyl or benzyl, A, B, C and D each represent CH, 1 or 2 of these CH groups optionally being replaced by N, $R^1$ represents a hydrogen atom or an alkyl, alkenyl or alkinyl radical, each having up to 18 carbon atoms, it being possible for the alkenyl and alkinyl radicals to contain 1, 2 or 3 double or triple bonds, or represents a monocyclic, aliphatic radical having 3 to 8 carbon atoms, a bicyclic or tricyclic radical with up to 14 carbon atoms, these cyclic alphatic radicals being saturated or singly or doubly unsaturated, or represents an optionally substituted phenyl or benzyl radical, it being possible for the alkyl, alkenyl and alkinyl radicals mentioned to be substituted by substituents from: hydroxyl, alkoxy (preferably having 1 to 4 carbon atoms, especially methoxy or ethoxy), aryloxy (particularly phenoxy, it being possible for the phenyl radical thereof optionally being substituted by $NO_2$, amino, acetamido, $C_1$ to $C_4$ alkyl, $C_1$ to $C_4$ alkoxy, halogen, $CF_3$, carboxyl or carboalkoxy (having 1 to 4 carbon atoms in the alkoxy radical), acyloxy or monoacylamino, the acyl radical thereof in each case being derived from an aliphatic (particularly alkanoic) carboxylic acid having 1 to 7 carbon atoms, an aromatic carboxylic acid (particularly a phenylcarboxylic acid which is optionally substituted in the phenyl radical by OH, halogen, particularly F, Cl or Br, $C_1$ to $C_4$ alkyl, $C_1$ to $C_4$ alkoxy, nitro and/or amino) or a heterocyclic carboxylic acid which is derived from a 5-membered or 6-membered heterocyclic structure which contains 1 to 3 hetero-atoms (N, O or S) and is optionally substituted in the heterocyclic ring by $C_1$ to $C_4$ alkyl, chlorine, bromine or amino, further from amino, monoalkylamino and dialkylamino (preferably having 1 to 4 carbon atoms per alkyl radical, particularly monomethylamino, monoethylamino, dimethylamino and diethylamino), mercapto, alkylthio preferably having 1 to 4 carbon atoms (particularly methylthio and ethylthio), halogen (preferably fluorine, chlorine and bromine), alkylcarbonyl (preferably having 1 to 4 carbon atoms in the alkyl radical), carboxyl, nitro, cyano, —CHO group, a sulphonic acid group, a heterocyclic substituent (e.g. phthalimido, pyridyl, thienyl, furyl, isoxazolyl and thiazolyl), and an aromatic radical (such as naphthyl and particularly phenyl, which can carry one or several, preferably 1, 2 or 3, identical or different substituents selected from —OH, —$NH_2$, $C_1$-$C_4$—alkyl—NH—, $C_1$-$C_4$—dialkyl—N—, $C_1$-$C_4$—alkoxy, $NO_2$, —CN, —COOH, —COO—alkyl ($C_1$-$C_4$), $C_1$-$C_6$—alkyl, halogen, particularly fluorine, chlorine or bromine, $C_1$-$C_4$—alkylthio, —SH, $C_1$-$C_4$—alkylsulphonyl, —$SO_3H$, —$SO_2$—$NH_2$ and —$SO_2$—NH— alkyl ($C_1$-$C_4$)) or the alkyl radical $R^1$ can also carry a monocyclic, bicyclic or tricyclic substituent (preferably having 3 to 10 carbon atoms) which in turn is optionally substituted by hydroxyl, amino, halogen, particularly fluorine, chlorine or bromine, or —COOH.

$R^2$, $R^3$ and $R^4$ are identical or different, and each represents a hydrogen atom, a $C_1$ to $C_6$ alkyl or alkenyl radical, a phenyl, $C_1$ to $C_6$ alkoxy, phenoxy, $C_1$ to $C_6$ alkylthio, phenylthio, $C_1$ to $C_6$ alkylsulphonyl, phenylsulphonyl, acetyl, benzoyl, trifluoromethyl, trifluoromethoxy, trifluoromethylthio, hydroxymethyl, aminomethyl, ($C_1$ to $C_6$ alkyl)-carbonyloxymethyl ($C_1$ to $C_4$-alkyl)carbonylaminomethyl or benzyl radical, a benzyl radical which is substituted by OH, halogen, $C_1$ to $C_4$ alkyl, $C_1$ to $C_4$ alkoxy, nitro or amino, a phenethyl, mercapto, hydroxyl, $C_1$ to $C_4$ alkylcarbonyloxy, benzoyloxy or amino radical, a monoalkylamino or dialkylamino radical, with 1 to 4 carbon atoms in each alkyl radical, an acylamino radical, the acyl radical thereof being derived from an aliphatic carboxylic (particularly an alkanoic or alkenoic) acid having 1 to 12 carbon atoms, an aromatic carboxylic acid (particularly phenylcarboxylic acids which is optionally substituted in the phenyl radical by OH, halogen, particularly F, Cl or Br, $C_1$ to $C_4$—alkyl, $C_1$ to $C_4$ alkoxy, nitro or amino) or a heterocyclic carboxylic acid which are derived from a 5-membered or 6-membered heterocyclic structure which contains 1 to 3 hetero-atoms (N, O or S) and is optionally substituted in the heterocyclic ring by $C_1$-$C_4$—alkyl, chlorine, bromine or amino, a ($C_1$ to $C_6$ alkoxy)-carbonylamino radical, or a urea or thiourea radical, wherein the second nitrogen atom is optionally substituted by a $C_1$ to $C_{12}$ alkyl or phenyl, or by phenyl which is substituted by halogen, $C_1$ to $C_4$ alkyl, $C_1$ to $C_4$ alkoxy, $CF_3$ or $NO_2$, represents a sulphonylamino radical, the sulphonyl radical being derived from an aliphatic sulphonic acid (particularly an alkyl sulphonic acid) having 1 to 6 carbon atoms or an aromatic sulphonic acid (particularly a phenylsulphonic acid, the phenyl radical of which can be substituted by $NO_2$, amino, acetamido, $C_1$ to $C_4$ alkyl, $C_1$ to $C_4$ alkoxy, halogen or $CF_3$), a carboxyl radical, a carboalkoxy radical derived from a $C_1$ to $C_{12}$ alcohol, a carboxamido radical of ammonia, of a $C_1$ to $C_{12}$ aliphatic, primary or secondary amine, (such as dimethylamine, n-butylamine, n-octylamine) of a heterocyclic amine (such as pyrrolidine, morpholine or piperazine) or of an aromatic amine, (particularly an aniline, which is optionally substituted by halogen, $C_1$ to $C_4$ alkyl or $C_1$ to $C_4$ alkoxy), a sulphonic acid group, a sulphonamido radical of ammonia, of a $C_1$ to $C_{12}$ primary or secondary amine, (such as dimethylamine, n-butylamine, n-octylamine) of a heterocyclic amine (such as pyrrolidine, piperidine, piperazine or morpholine) or of an aromatic amines (particularly an aniline, which is optionally substituted by halogen, $C_1$ to $C_4$—alkyl or $C_1$ to $C_4$—alkoxy) or a fluorine, chlorine or bromine atom or a nitro radical.

Preferred starting compounds for the production of the active compounds of the present invention are compounds of formula (II), (III), (IV) and (V) in which the respective radicals X, A, B, C, D, $R^1$, $R^2$, $R^3$ and $R^4$ have the meanings given above in the description of the preferred active compounds of the present invention.

The present invention further provides, as new compounds, compounds of the formula (I) in which, X, $R^1$, $R^2$, $R^3$, $R^4$, A, B, C and D have the meanings given above except that (a) $R^1$ represents an optionally substituted straight-chain, branched, cyclic, saturated or unsaturated aliphatic hydrocarbon radical, an aryl radical or aralkyl radical as defined above, and, when X denotes an ethylene group, A, B, C and D each represent a CH group and $R^1$ denotes hydrogen, methyl or p-fluorobenzyl and (b) $R^2$ has any of those meanings given for $R^2$ in formula (I) other than a hydrogen atom, and when X denotes an ethylene group, A, B, C and D each represent a CH group and $R^1$ denotes hydrogen, methyl or p-fluorobenzyl.

Of particular interest are new compounds according to the present invention of the formula

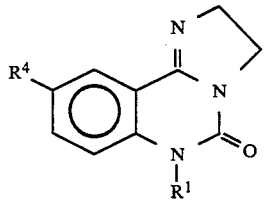

(I')

in which $R^1$ has the same meaning as in formula (I), and $R^4$ represents an acylamino radical, the acyl radical thereof being derived from an aliphatic carboxylic acid (particularly an alkane or alkene carboxylic acid) having 1 to 12 carbon atoms, an aromatic carboxylic acid (particularly a phenylcarboxylic acid which is optionally substituted in the phenyl radical by OH, halogen, particularly F, Cl or Br, $C_1$ to $C_4$—alkyl, $C_1$ to $C_4$ alkoxy, nitro or amino), or a heterocyclic carboxylic acid which is derived from a 5-membered or 6-membered heterocyclic structure which contains 1 to 3 heteroatoms (N, O or S) and is optionally substituted in the heterocyclic ring by $C_1$ to $C_4$ alkyl, chlorine, bromine or amino), a ($C_1$ to $C_6$ alkoxy)carbonylamino, or a urea or thiourea radical, wherein the second nitrogen atom is optionally substituted by $C_1$ to $C_{12}$ alkyl, or phenyl, or by phenyl which is substituted by halogen, $C_1$ to $C_4$ alkyl, $C_1$ to $C_4$-alkoxy, $CF_3$ or $NO_2$, or a sulphonylamino radical, the sulphonyl radical thereof being derived from an aliphatic, (particularly, alkane) sulphonic acid having 1 to 6 carbon atoms or an aromatic sulphonic acid (particularly a phenylsulphonic acid, the phenyl radical of which is optionally substituted by $NO_2$, amino, acetamido, $C_1$ to $C_4$ alkyl, $C_1$ to $C_4$ alkoxy, halogen or $CF_3$).

In the preparation of the active compounds and new compounds according to the present invention, instead of the anthranilic acids of the formula (II) and the carbonic acid esters of the formula (III) defined above, the isatoic anhydrides of the formula

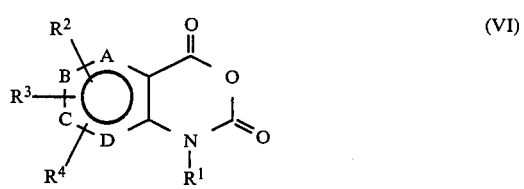

in which $R^1$, $R^2$, $R^3$, $R^4$, A, B, C and D have the meanings given above, can, if desired, be employed directly in the reaction according to the present invention.

If, for example, the reaction is carried out using anthranilic acid, phenylchlorocarbonate and ethylenediamine as the starting materials, the process can be illustrated by the following equation:

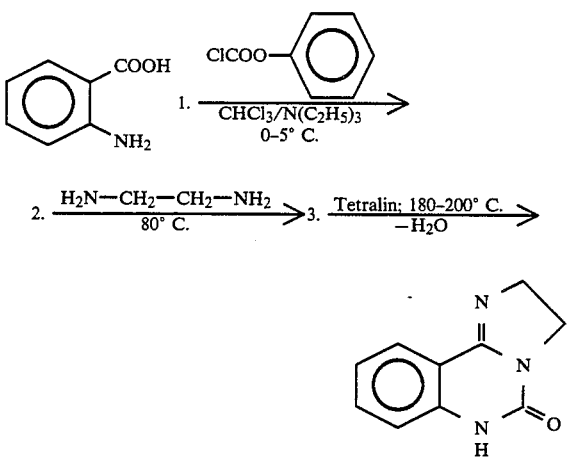

A further variant of the process for the preparation of those compounds in which $R^1$ does not denote hydrogen consists in subsequently treating compounds of the general formula (I) in which $R^1$ represents a hydrogen atom with an agent which replaces the hydrogen atom by a hydrocarbyl or acyl radical.

If, for example, 5-oxo-2,3,5,6-tetrahydroimidazo-[1,2-c]-quinazoline and allyl bromide are used as starting materials, the process can be illustrated by the following equation:

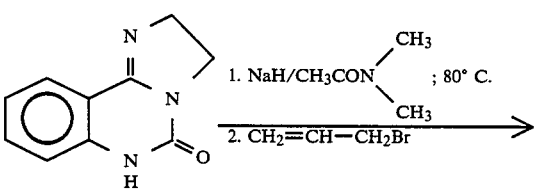

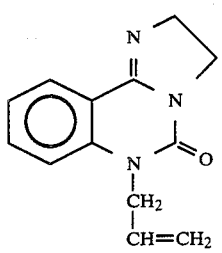

A further variant of this process (replacement of a hydrogen atom by another radical, in this instance an benzylic radical, under phase transfer conditions) is illustrated by the following equation:

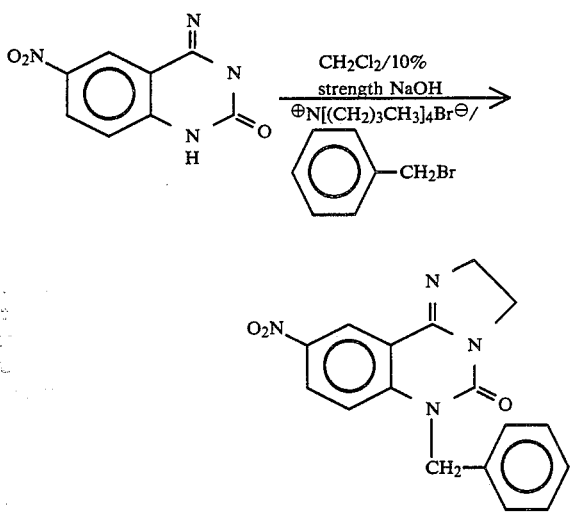

Furthermore, it has been found that compounds in which $R_3$ and/or $R_4 \neq H$ are obtained by an electrophilic substitution reaction for an aromatic nucleus, using compounds of the formula (I), in which A, B, C and D are CH and $R_2$, $R_3$ and $R_4 = H$, as starting materials.

This process may be illustrated, for example, with reference to the following equation:

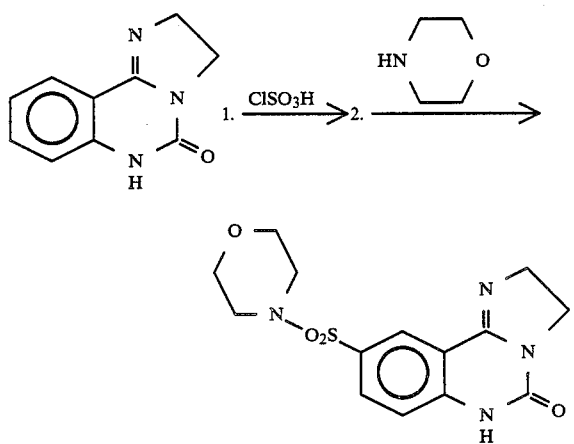

The compounds which are obtained and which have functional radicals in the aromatic ring can then be transformed in many ways, as the example shows, according to customary methods.

The reaction of the anthranilic acid of formula (II) with the chlorocarbonic acid ester of formula (III) is effected in inert aprotic solvents, with the addition of an acid-binding agent. The following may be mentioned as examples of such solvents: chloroform, methylene chloride, tetrahydrofuran, dioxane, diethyl ether, benzene and toluene.

A tertiary amine, for example triethylamine, is preferably used as the acid-binding agent. However, alkali metal carbonates or bicarbonates can also be used.

The reaction can be carried out at a temperature between $-20°$ and $150°$ C., particularly at the boiling point of the solvent. The reaction is preferably carried out at a temperature between $10°$ and $180°$ C., particularly at room temperature.

After the end of the reaction, the solvent is stripped off, or, if the reaction product is not readily soluble in the solvent used, the reaction product is isolated by filtration.

The salts are then removed by stirring the mixture with water, and the intermediate product is dried.

The further reaction with the diamine (IV) can be effected using an excess of the diamine as a solvent. However, it can also be carried out using an equimolar quantity of the diamine in an inert aprotic solvent. The reaction is carried out between room temperature ($20°$ C.) and $150°$ C., preferably between $60°$ and $100°$ C.

Excess amine and/or solvent is then removed in a rotary evaporator, and an inert high-boiling solvent is added to the reaction. Tetralin is preferably used as the solvent in this case. The contents of the flask are heated to temperatures between $150°$ and $250°$ C., preferably $180°$ to $210°$ C., water, residual diamine and solvent, for example tetralin, being distilled off.

For the conversion of the compounds of the formula (I) in which $R_1 = H$ into compounds in which $R_1$ has another of its meanings with the agents of formula $R_1-Z$, the anion is first formed, for example, using NaH in an inert aprotic solvent (such as dimethylformamide, dimethylacetamide, dimethylsulphoxide or hexamethylphosphoric acid triamide) and this anion is then reacted with the alkylating agent. The formation of the anion is effected at a temperature between $0°$ and $100°$ C., preferably at a temperature between $40°$ and $80°$ C. The reaction of the anion with the alkylating agent is carried out at a temperature between $0°$ and $100°$ C., preferably between room temperature and $80°$ C.

The above-mentioned conversion can also be carried out in a two-phase system under the conditions of phase transfer catalysts. One phase is an inert, water-immiscible organic solvent (such as methylene chloride, benzene or toluene), and the other phase is an aqueous phase in which a strong inorganic base is dissolved. 5 to 40% strength aqueous sodium hydroxide or potassium hydroxide solutions are examples of a suitable aqueous phase, and a 10 to 20% strength sodium hydroxide solution is preferably used. The reaction is carried out at a temperature between $20°$ and $80°$ C. A quaternary ammonium salt (such as tetra-n-butylammonium bromide or benzyl-tri-n-butylammonium bromide) can be used as the phase transfer catalyst.

The anthranilic acids, chlorocarbonic acid esters, diamines and reactive alkylating agents used are known or can be prepared according to processes known from the literature (see Rodd's Chemistry of Carbon Compounds, Second Edition, Volume III, Part 6, page 49 et seq.; Houben-Weyl, 4th Edition, Volume 7/4, pages 30 and 32; Houben-Weyl, 4th Edition, Volume 8, page 75 et seq; Houben-Weyl, 4th Edition, Volume 11/1; Houben-Weyl, 4th Edition, Volume 5/4; and Houben-Weyl, 4th Edition, Volume 9, pages 388 and 389).

The compounds of the formula (I) for use in compositions according to the invention surprisingly show a series of advantageous pharmacological actions, in particular, they affect the circulation. In detail, they cause a strong increase in contractility (positive inotropic action) in isolated myocardial preparations, and lead, in vivo, to a considerable increase in the rate of tension of the left ventricle of the heart, as well as the systolic volume and heart minute volume, without thereby increasing the blood pressure. They are, therefore, particularly suitable for treating congestive heart failure. With a knowledge of the state of the art, it could not be expected that this class of substance would show such an advantageous action on the circulation.

As stated above, the invention also relates to the use in medicine of the compounds of the invention.

The present invention provides pharmaceutical compositions containing as active ingredient a compound of the invention in admixture with an inert pharmaceutical carrier, i.e., a solid or liquefied gaseous diluent, or a liquid diluent other than a solvent of a molecular weight less than 200 (preferably less than 350) except in the presence of a surface active agent.

The invention further provides pharmaceutical compositions containing as active ingredient a compound of the invention in the form of a sterile and/or physiologically isotonic aqueous solution.

The invention also provides medicaments in dosage unit form comprising a compound of the invention.

The invention also provides medicaments in the form of tablets (including lozenges and granules), dragees, capsules, pills, ampoules or suppositories comprising a compound of the invention.

"Medicament" as used in this Specification means physically discrete coherent portions suitable for medical administration. "Medicament in dosage unit form" as used in this Specification means physically discrete coherent units suitable for medical administration each containing a daily dose or a multiple (up to four times) or sub-multiple (down to a fortieth) of a daily dose of the compound of the invention in association with a carrier and/or enclosed within an envelope. Whether the medicament contains a daily dose or, for example, a half, a third or a quarter of a daily dose will depend on whether the medicament is to be administered once or, for example, twice, three times or four times a day respectively.

The pharmaceutical composition according to the invention may, for example, take the form of suspensions, solutions and emulsions of the active ingredient in aqueous or non-aqueous diluents or syrups.

The diluents to be used in pharmaceutical compositions (e.g. granulates) adapted to be formed into tablets, dragees, capsules and pills include the following:

(a) fillers and extenders, e.g. starch, sugars, mannitol, and silicic acid; (b) binding agents, e.g. carboxymethyl cellulose and other cellulose derivatives, alginates, gelatine and polyvinyl pyrrolidone; (c) moisturizing agents, e.g. glycerol; (d) disintegrating agents, e.g. agar-agar, calcium carbonate and sodium bicarbonate; (e) agents for retarding dissolution e.g. paraffin; (f) resorption accelerators, e.g. quaternary ammonium compounds; (g) surface active agents, e.g. cetyl alcohol, glycerol monostearate; (h) adsorptive carriers, e.g. kaolin and bentonite; (i) lubricants, e.g. talc, calcium and magnesium stearate and solid polyethyl glycols.

The tablets, dragees, capsules and pills formed from the pharmaceutical compositions of the invention can have the customary coatings, envelopes and protective matrices, which may contain opacifiers. They can be so constituted that they release the active ingredient or preferably in a particular part of the intestinal tract, possibly over a period of time. The coatings, envelopes and protective matrices may be made, for example, of polymeric substances or waxes.

The ingredient can also be made up in microencapsulated form together with one or several of the above-mentioned diluents.

The diluents to be used in pharmaceutical compositions adapted to be formed into suppositories can, for example, be the usual water-soluble diluents, such as polyethylene glycols and fats (e.g. cocoa oil and high esters (e.g. $C_{14}$-alcohol with $C_{16}$-fatty acid)) or mixtures of these diluents.

The pharmaceutical compositions which are solutions and emulsions can, for example, contain the customary diluents (with, of course, the above-mentioned exclusion of solvents having a molecular weight below 200 except in the presence of a surface-active agent), such as solvents, dissolving agents and emulsifiers; specific examples of such diluents are water, ethyl alcohol, isopropyl alcohol, ethyl carbonate, ethyl acetate, benzyl alcohol, benzyl benzoate, propylene glycol, 1,3-butylene glycol, dimethylformamide, oils (for example ground nut oil), glycerol, tetrahydrofurfuryl alcohol, polyethylene glycols and fatty acid esters of sorbitol or mixtures thereof.

For parenteral administration, solutions and emulsions should be sterile, and, if appropriate, blood-isotonic.

The pharmaceutical compositions which are suspensions can contain the usual diluents, such as liquid diluents, e.g. water, ethyl alcohol, propylene glycol, surface-active agents (e.g. ethoxylated isostearyl alcohols, polyoxyethylene sorbite and sorbitane esters), microcrystalline cellulose, aluminium metahydroxide, bentonite, agar-agar and tragacanth or mixtures thereof.

All the pharmaceutical compositions according to the invention can also contain colouring agent and preservatives as well as perfumes and flavouring additions (e.g. peppermint oil and eucalyptus oil) and sweetening agents (e.g. saccharin).

The pharmaceutical compositions according to the invention generally contain from 0.1 to 99.5% usually from 0.5 to 95% of the active ingredient by weight of the total composition.

In addition to a compound of the invention, the pharmaceutical compositions and medicaments according to the invention can also contain other pharmaceutically active compounds. They may also contain a plurality of compounds of the invention.

Any diluent in the medicaments of the present invention may be any of those mentioned above in relation to the pharmaceutical compositions of the present invention. Such medicaments may include solvents of molecular weight less than 200 as sole diluent.

The discrete coherent portions constituting the medicament according to the invention will generally be adapted by virtue of their shape or packaging for medical administration and may be, for example, any of the following: tablets (including lozenges and granulates), pills, dragees, capsules, suppositories and ampoules. Some of these forms may be made up for delayed release of the active ingredient. Some, such as capsules, include a protective envelope which renders the portions of the medicament physically discrete and coherent.

The preferred daily dose for administration of the medicaments of the invention is 50 mg to 2.5 g of active ingredient.

The production of the above-mentioned pharmaceutical compositions and medicaments is carried out by any method known in the art, for example, by mixing the active ingredient(s) with the diluent(s) to form a pharmaceutical composition (e.g. a granulate) and then forming the composition into the medicament (e.g. tablets).

This invention further provides a method of combating the above-mentioned diseases in warm-blooded animals, which comprises administering to the animals a compound of the invention alone or in admixture with a diluent or in the form of a medicament according to the invention.

It is envisaged that these active compounds will be administered perorally, parenterally (for example intramuscularly, intraperitoneally, subcutaneously and intravenously) or rectally, preferably orally. Preferred pharmaceutical compositions and medicaments are therefore those adapted for administration such as oral administration. Administration in the method of the invention is preferably oral administration.

In general it has proved advantageous to administer orally amounts of from 0.1 mg to 100 mg/kg, preferably 1.0 mg to 50 mg/kg, of body weight per day to achieve effective results. Generally the administration is distributed over 1 to 6 administrations, in particular before and/or during and/or after meals. An individual administration preferably contains the active compound or compounds in amounts of 1.0 to 20 mg/kg of body weight. Nevertheless, it can at times be necessary to deviate from those dosage rates, and in particular to do so as a function of the nature and body weight of the subject to be treated, the individual reaction of this subject to the treatment, the type of formulation in which the active ingredient is administered and the mode in which the administration is carried out, and the point in the progress of the disease or interval at which it is to be administered. Thus it may in some case suffice to use less than the abovementioned minimum dosage rate, whilst other cases the upper limit mentioned must be exceeded to achieve the desired results. Where larger amounts are administered it can be advisable to divide these into several individual administrations over the course of the day.

The positive inotropic action of the active compounds used according to the present invention was found in guineapig auricles and isolated perfused guineapig hearts. For this purpose, after the animals had been killed by a blow to the neck and after excission of the hearts, the left auricles were suspended in a thermostatically controlled bath at 30° C. containing a Krebs-Henseleit solution treated with carbogen gas, and the isometric development of tension of the auricles, which were electrically stimulated with 1 hertz, was registered via a Statham pressure transducer before and 14 minutes after addition of the substances to be investigated. The investigations on isolated perfused guineapig hearts were carried out by a modification of the method according to Opie (see L. Opie, J. Physiol. 180 (1965), 529–541). The hearts were perfused retrogradely through the aorta and the coronary arteries with 10 ml of Krebs-Henseleit solution, saturated with carbogen, per minute, and after a latex balloon, which was filled with liquid and which was connected to a Statham pressure transducer, was introduced into the left ventricle, the isovolumetric development of tension was measured. It was found that the compounds of the general formula (I) according to the invention have a positive inotropic action in the range of $10^{-7}$ to $10^{-4}$ g/ml on the isolated organs described above, in the presence and in the absence of the beta receptor blocker propranolol.

In a cat anaesthetised with pentobarbital, these compounds increase the rate of tension of the left ventricle of the heart, particularly after intraduodenal administration in the range of 0.1 to 10 mg/kg. During this treatment, the systemic blood pressure is not increased, but is even slightly lowered. In addition, the active compounds for use according to the present invention also lead to an inhibition of thrombocyte aggregation, which can be advantageous in the case of cardiac insufficiency due to ischemic heart areas.

These advantageous actions thus represent an enrichment of pharmacy.

The following Examples illustrate the production of active compounds for use in pharmaceutical compositions of the present invention.

EXAMPLE 1

5-Oxo-2,3,5,6-tetrahydroimidazo-[1,2,-c]-quinazoline

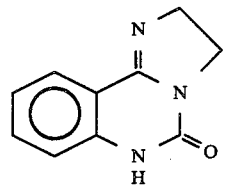

46 g (0.33 mol) of anthranilic acid and 45 ml of triethylamine were dissolved in 300 ml of CHCl$_3$, and a solution of 57 g (0.33 mol + 10%) of phenylchloroformate in 100 ml of CHCl$_3$ was added dropwise at a temperature between 0° and 5° C. to the first solution. The reaction mixture was stirred overnight at room temperature. The solvent was then stripped off in a rotary evaporator, without separating off the precipitated product. The residue was thoroughly stirred with water and was then filtered off under suction. After the crude product (76 g) had been dried, it was used for further reaction. 76 g of the crude product were added in portions to 150 ml of ethylenediamine and the mixture was then further stirred at 80° C. for another 20 minutes. The excess ethylenediamine was stripped off in a rotary evaporator, and 150 ml of tetralin were added to the residue. The mixture was heated in an oil bath (temperature: 200° to 240° C.) and water which was formed, excess ethylenediamine and tetralin were distilled off, until the internal temperature had increased to approximately 190° C. (30 to 60 minutes). 100 ml of ethanol were added dropwise to the solution, which was still warm, and the mixture was allowed to crystallise out. The deposit was filtered off under suction, and then washed with alcohol and ether, and thoroughly stirred with 150 ml of dimethylformamide for 1 hour. The mixture was again filtered under suction, and the residue was then washed with alcohol and dried.

Yield: 25 g=40% (relative to anthranilic acid employed);
Melting point: 295° C.

For further purification, the product could be recrystallised from dimethylformamide. Melting point: 298° to 300° C.

The following compounds were prepared analogously to Example 1:

EXAMPLE 2

9-Chloro-5-oxo-2,3,5,6-tetrahydroimidazo-[1,2-c]-quinazoline

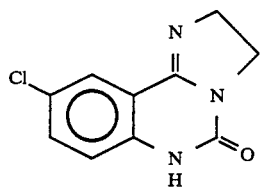

Melting point: >300° C.

EXAMPLE 3

9-Fluoro-5-oxo-2,3,5,6-tetrahydroimidazo-[1,2-c]-quinazoline

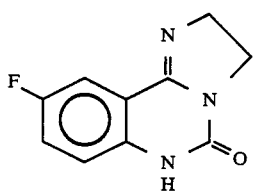

Melting point: >310° C.;
Yield: 41%.

EXAMPLE 4

10-Chloro-5-oxo-2,3,5,6-tetrahydroimidazo-[1,2-c]-quinazoline

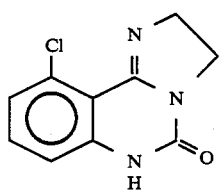

Melting point: 330° C.

EXAMPLE 5

7,9-Dichloro-5-oxo-2,3,5,6-tetrahydroimidazo-[1,2-c]-quinazoline

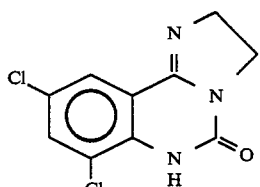

Melting point: 298°–299° C.

EXAMPLE 6

9-Methyl-5-oxo-2,3,5,6-tetrahydroimidazo-[1,2-c]-quinazoline

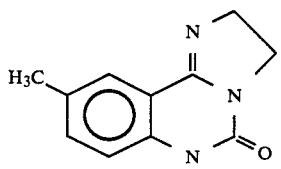

Melting point: 310°–313° C.

EXAMPLE 7

8,10-Dimethyl-5-oxo-2,3,5,6-tetrahydroimidazo-[1,2-c]-quinazoline

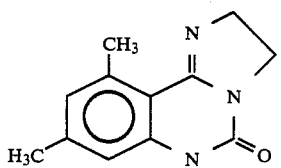

Melting point: 270° C.

EXAMPLE 8

9-Trifluoromethyl-5-oxo-2,3,5,6-tetrahydroimidazo-[1,2-c]-quinazoline

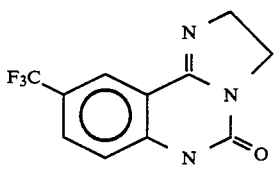

Melting point: 295°–298° C.;
Yield: 23%.

EXAMPLE 9

8-Trifluoromethyl-5-oxo-2,3,5,6-tetrahydroimidazo-[1,2-c]-quinazoline

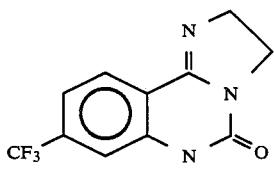

Melting point: >310° C.;
Yield: 10%.

EXAMPLE 10

9-Trifluoromethoxy-5-oxo-2,3,5,6-tetrahydroimidazo-[1,2-c]-quinazoline

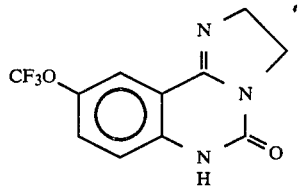

Melting point: 272°–274° C.;
Yield: 42%.

EXAMPLE 11

8,9-Dimethoxy-5-oxo-2,3,5,6-tetrahydroimidazo-[1,2-c]-quinazoline

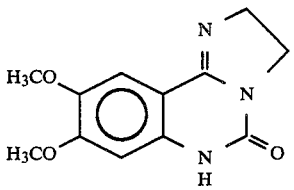

Melting point: 283° C.;
Yield: 36%.

EXAMPLE 12

7,8,9-Trimethoxy-5-oxo-2,3,5,6-tetrahydroimidazo-[1,2-c]-quinazoline

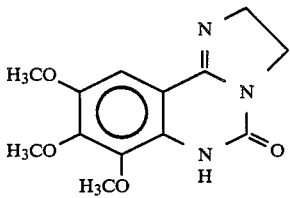

Melting point: 237° C.

EXAMPLE 13

6-Methoxy-,9-chloro-,10-methyl-5-oxo-2,3,5,6-tetrahydroimidazole-[1,2-c]-quinazoline

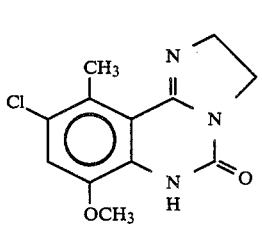

Melting point: 280°–286° C.

EXAMPLE 14

5-Oxo-2,3,5,6-tetrahydroimidazo-[1,2-c]-pyrido-[3,2-e]-pyrimidine

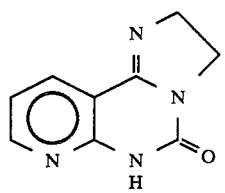

Melting point: 260° C.;
Yield: 10%.

EXAMPLE 15

5-Oxo-2,3,5,6-tetrahydroimidazo-[1,2-c]-pyrido-[2,3-e]-pyrimidine

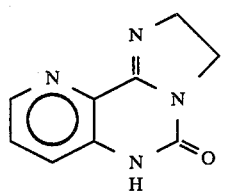

Melting point: >280° C.;
Yield: 18%.

EXAMPLE 16

7-Methoxy-8-methyl-5-oxo-2,3,5,6-tetrahydroimidazo-[1,2-c]-quinazoline

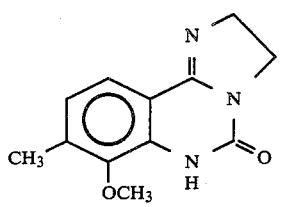

Melting point: 205°–210° C.

EXAMPLE 17

7,9-Dibromo-5-oxo-2,3,5,6-tetrahydroimidazo-[1,2-c]-quinazoline

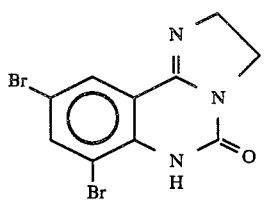

Melting point: 315° C.;
Yield: 43%.

EXAMPLE 18

7-Methyl-5-oxo-2,3,5,6-tetrahydroimidazo-[1,2-c]-quinazoline

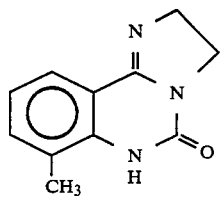

Melting point: 250°–255° C.;
Yield: 26%.

EXAMPLE 19

5-Oxo-6-allyl-2,3,5,6-tetrahydroimidazo-[1,2-c]-quinazoline

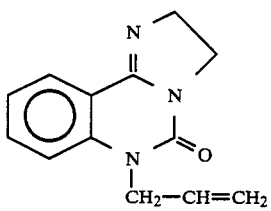

6.9 g (0.037 mol) of 5-oxo-2,3,5,6-tetrahydroimidazo-[1,2-c]-quinazoline in 60 ml of absolute dimethylacetamide were added to 1.75 g (0.058 mol) of an 80% strength suspension of NaH in oil (Schuchardt), after the suspension had been thoroughly stirred twice with 20 ml of n-hexane in each case and the solvent had been decanted, and the mixture was heated to 80° C. for 1 hour. During this process, a clear solution was gradually formed. The solution was cooled, and 4.6 ml (0.053 mol) of allyl bromide were added dropwise. The mixture was then heated to 100° C. for 4 hours. It was concentrated in a rotary evaporator to one third of its volume and was poured onto ice-water. The precipitated product was filtered off under suction and was recrystallised from methanol/water.

Yield: 4 g (48% of theory);
Melting point: 128°–131° C.

The following compounds were prepared analogously to Example 19:

EXAMPLE 20

5-Oxo-6-methyl-2,3,5,6-tetrahydroimidazo-[1,2-c]-quinazoline

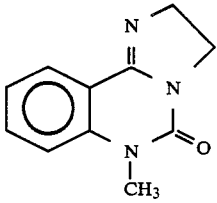

Melting point: 159°–163° C.;
Yield: 44%.

EXAMPLE 21

5-Oxo-6-n-butyl-2,3,5,6-tetrahydroimidazo-[1,2-c]-quinazoline

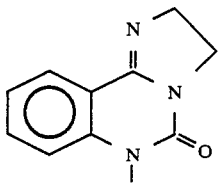

Melting point: 113°–115° C.;
Yield: 31%.

EXAMPLE 22

5-Oxo-6-diethylaminoethyl-2,3,5,6-tetrahydroimidazo-[1,2-c]-quinazoline

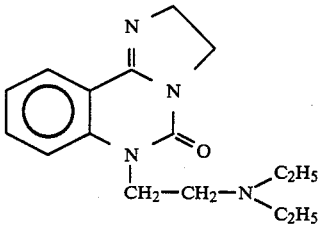

Melting point: 54°–57° C.;
Yield: 35%.

EXAMPLE 23

5-Oxo-6-benzyl-2,3,5,6-tetrahydroimidazo-[1,2-c]-quinazoline

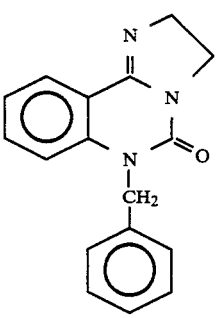

Melting point: 142°–144° C.;
Yield: 36%.

EXAMPLE 24

5-Oxo-6-[3,4-dichloro-α-methyl-benzyl]-2,3,5,6-tetrahydroimidazo-[1,2-c]-quinazoline

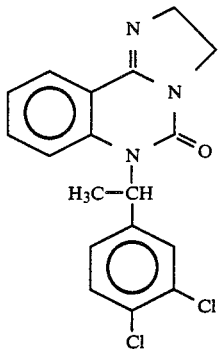

Melting point: 154°–157° C.

EXAMPLE 25

9-Nitro-5-oxo-6-methyl-2,3,5,6-tetrahydroimidazo-[1,2-c]-quinazoline

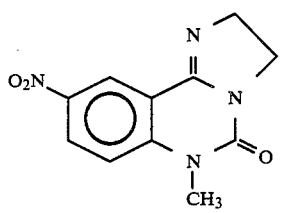

Melting point: 259°–260° C.;
Yield: 58%.

(9-Nitro-5-oxo-2,3,5,6-tetrahydroimidazo-[1,2-c]-quinazoline was used as the starting material).

EXAMPLE 26

5-Oxo-6-methyl-2,3,5,6-tetrahydroimidazo-[1,2-c]pyrido-[2,3-e]-pyrimidine

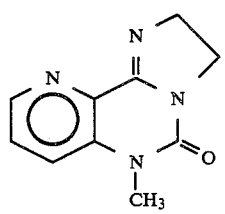

Melting point: 247°–250° C.;
Yield: 37%.

EXAMPLE 27

5-Oxo-6-allyl-2,3,5,6-tetrahydroimidazo-[1,2-c]-pyrido[2,3-e]-pyrimidine

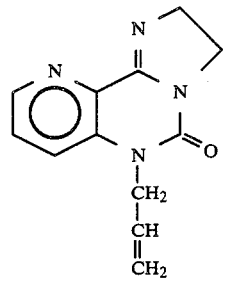

Melting point: 236° C.;
Yield: 20%.

EXAMPLE 28

5-Oxo-6-benzyl-2,3,5,6-tetrahydroimidazo-[1,2-c]-pyrido-[2,3-e]-pyrimidine

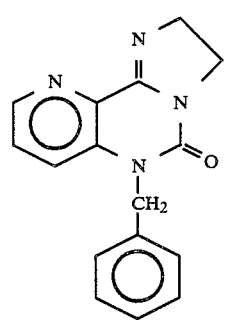

Melting point: 205°–207° C.;
Yield: 19%.

EXAMPLE 29

9-Nitro-5-oxo-6-benzyl-2,3,5,6-tetrahydroimidazo-[1,2-c]-quinazoline

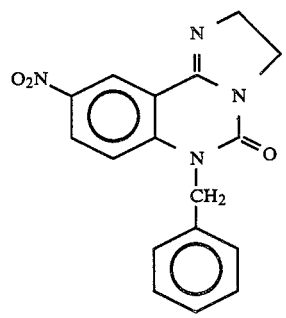

11.5 g (0.05 mol) of 9-nitro-5-oxo-2,3,5,6-tetrahydroimidazo-[1,2-c]-quinazoline and 6.4 g (0.02 mol) of tetra-n-butylammonium bromide were suspended in 250 ml of 10% strength sodium hydroxide solution. 17.815 g (0.15 mol) of benzyl bromide in 150 ml of methylene chloride were added to the mixture, and the latter was stirred for 2 hours at room temperature.

The organic phase was separated off, and the aqueous phase was extracted twice with CH$_2$Cl$_2$. The combined organic phases were washed twice with a little water and were dried. After the solvent had been removed, the residue was crystallised using ethanol, and the crystals were filtered off under suction. The crystals were recrystallised from methanol.

Yield: 8 g (50% of theory);
Melting point: 175°–177° C.

The following compounds were prepared analogously to Example 29:

EXAMPLE 30

9-Nitro-5-oxo-6-allyl-2,3,5,6-tetrahydroimidazo-[1,2-c]-quinazoline

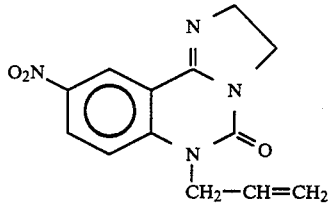

Melting point: 207°–209° C.;
Yield: 81%.

EXAMPLE 31

9-Nitro-5-oxo-2,3,5,6-tetrahydroimidazo-[1,2-c]-quinazoline

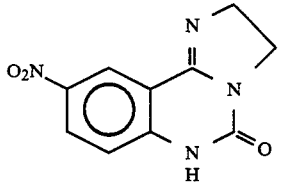

7 ml of concentrated $H_2SO_4$ were added, whilst cooling, to 5 ml of 98% strength $HNO_3$. 9.3 g (0.05 mol) of 5-oxo-2,3,5,6-tetrahydroimidazo-[1,2-c]-quinazoline were added in portions at 0° to 5° C. to this mixture, and the latter was stirred for 2 hours at room temperature. The reaction mixture was then poured into ice water, and the precipitated deposit was filtered off under suction. It was neutralised in water with $NaHCO_3$, the mixture being heated to boiling for a short time. After the mixture had been cooled, the precipitate was again filtered off under suction, washed with ethanol and ether, and dried.

Yield: 8.3 g (72% of theory);
Melting point: >300° C.

EXAMPLE 32

7,9-Dinitro-5-oxo-2,3,5,6-tetrahydroimidazo-[1,2-c]-quinazoline

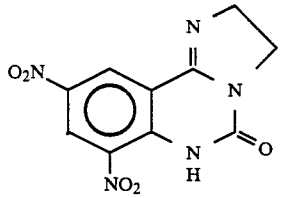

If the reaction time was extended to 24 hours under the conditions given above in Example 31, the dinitro compound was mainly obtained.

Melting point: 225°–226° C.

EXAMPLE 33

9-Amino-5-oxo-2,3,5,6-tetrahydroimidazo-[1,2-c]-quinazoline

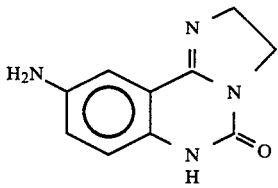

4.6 g of 9-nitro-5-oxo-2,3,5,6-tetrahydroimidazo-[1,2-c]-quinazoline were dissolved in 4.8 g (0.12 mol) of NaOH in 80 ml of $H_2O$. 10.5 g of sodium dithionite were added to the mixture, during which the temperature increased to 60° C. The mixture was then heated to boiling for a short time. After the mixture had been cooled, the precipitated crystals were filtered off under suction, washed with $H_2O$ and finally thoroughly stirred in 1N NaOH. The mixture was then again filtered off under suction, and the residue was washed with water, ethanol and ether, and dried.

Yield: 3.3 g (82% of theory);
Melting point: >300° C.

The following compounds were prepared analogously to Example 33:

EXAMPLE 34

9-Amino-5-oxo-6-allyl-2,3,5,6-tetrahydroimidazo-[1,2-c]-quinazoline

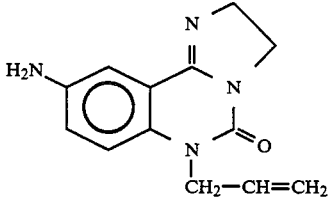

Melting point: 183°–184° C.;
Yield: 31%.

EXAMPLE 35

9-Amino-5-oxo-6-benzyl-2,3,5,6-tetrahydroimidazo-[1,2-c]-quinazoline

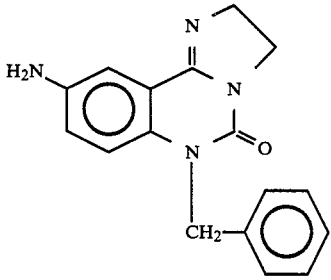

Melting point: 195°–198° C.;

Yield: 20%.

EXAMPLE 36

9-Amino-5-oxo-6-methyl-2,3,5,6-tetrahydroimidazo-[1,2-c]-quinazoline

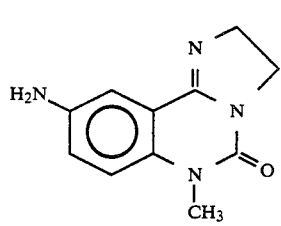

Melting point: 273°–275° C.;
Yield: 11%.

EXAMPLE 37

9-Isovaleroylamino-5-oxo-2,3,5,6-tetrahydroimidazo-[1,2-c]-quinazoline

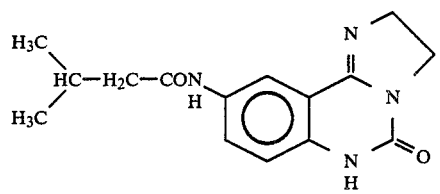

2.5 g (0.02 mol) of isovaleric acid chloride were added to 2.02 g (0.01 mol) of 9-amino-5-oxo-2,3,5,6-tetrahydroimidazo-[1,2-c]-quinazoline in 30 ml of absolute pyridine, and the mixture was stirred for 8 hours at room temperature. The mixture was then diluted with ether, and the precipitated crystals were separated off. The crystals were dissolved in water, the aqueous solution was purified with active charcoal and the free base was then precipitated by the addition of ammonia. It was filtered off under suction and dried.

Yield: 1.4 g (49% of theory);
Melting point: >305° C.

The following compounds were prepared analogously to Example 37:

EXAMPLE 38

9-Acetamido-5-oxo-2,3,5,6-tetrahydroimidazo-[1,2-c]-quinazoline

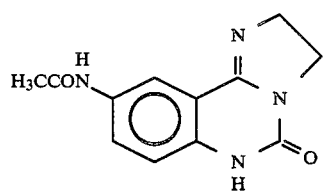

Melting point: >300° C.;
Yield: 49%.

EXAMPLE 39

9-Propionylamino-5-oxo-2,3,5,6-tetrahydroimidazo-[1,2-c]-quinazoline

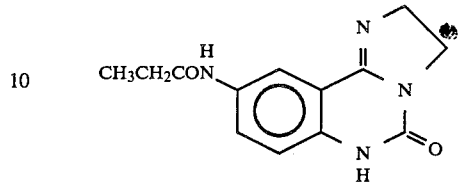

Melting point: >305° C.;
Yield: 50%.

EXAMPLE 40

9-n-Valeroylamino-5-oxo-2,3,5,6-tetrahydroimidazo-[1,2-c]-quinazoline

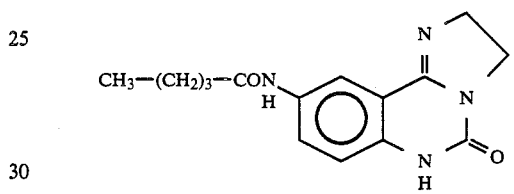

Melting point: 298°–300° C.;
Yield: 35%.

EXAMPLE 41

9-Nonanoylamino-5-oxo-2,3,5,6-tetrahydroimidazo-[1,2-c]-quinazoline

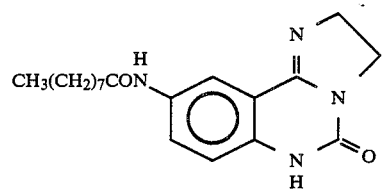

Melting point: 268°–270° C.;
Yield: 93%.

EXAMPLE 42

9-Acetylamino-5-oxo-6-allyl-2,3,5,6-tetrahydroimidazo-[1,2-c]-quinazoline

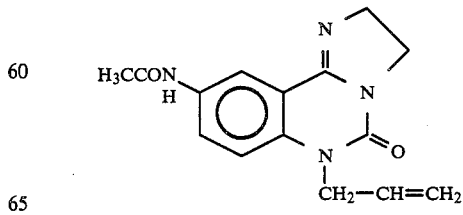

Melting point: 232°–234° C.;
Yield: 32%.

EXAMPLE 43

9-Propionylamino-5-oxo-6-allyl-2,3,5,6-tetrahydroimidazo-[1,2-c]-quinazoline

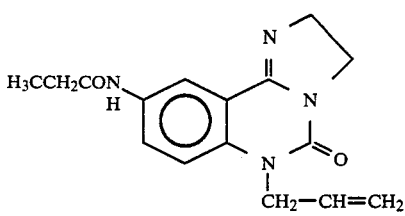

Melting point: 149°–152° C.;
Yield: 63%.

EXAMPLE 44

9-Isovaleroylamino-5-oxo-6-allyl-2,3,5,6-tetrahydroimidazo-[1,2-c]-quinazoline

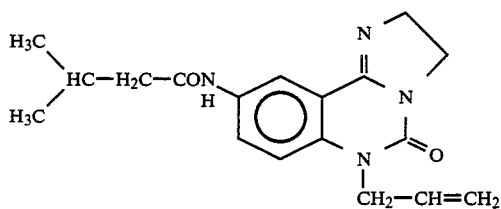

Melting point: 202°–205° C.;
Yield: 73%.

The following compounds were prepared analogously to Example 37 using the appropriate chlorocarbonic acid esters:

EXAMPLE 45

9-Methoxycarbonylamino-5-oxo-2,3,5,6-tetrahydroimidazo-[1,2-c]-quinazoline

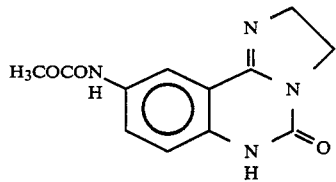

Melting point: >300° C.;
Yield: 97%.

EXAMPLE 46

9-Ethoxycarbonylamino-5-oxo-2,3,5,6-tetrahydroimidazo-[1,2-c]-quinazoline

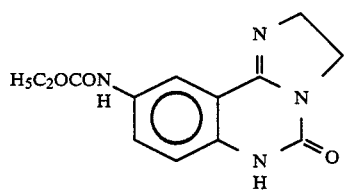

Melting point: 300° C.;
Yield: 98%.

EXAMPLE 47

9-i-Butyloxycarbonylamino-5-oxo-2,3,5,6-tetrahydroimidazo-[1,2-c]-quinazoline

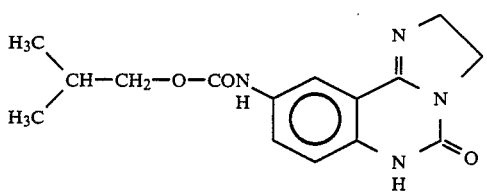

Melting point: 300° C.;
Yield: 43%.

EXAMPLE 48

9-N'-Methylureido-5-oxo-2,3,5,6-tetrahydroimidazo-[1,2-c]-quinazoline

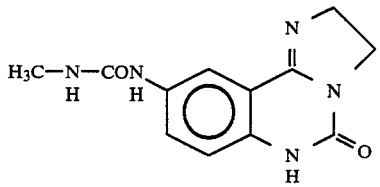

5 ml of methyl isocyanate were added to 2.02 g (0.01 mol) of 9-amino-5-oxo-2,3,5,6-tetrahydroimidazo-[1,2-c]-quinazoline and 2 drops of tin octoate in 30 ml of pyridine at room temperature. The mixture was then heated to 80° C. for 1 hour. After the mixture had been cooled, the reaction product was precipitated from the solution using ether, and was filtered off under suction. It was thoroughly stirred with water, again filtered off under suction and dried.

Yield: 1.7 g (66% of theory);
Melting point: >300° C.

The following compounds were prepared analogously to Example 48:

EXAMPLE 49

9-N'-n-Propylureido-5-oxo-2,3,5,6-tetrahydroimidazo-[1,2-c]-quinazoline

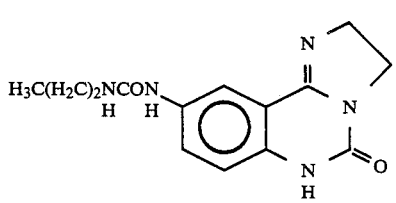

Melting point: >300° C.;
Yield: 59%.

EXAMPLE 50

9-N′-Phenylureido-5-oxo-2,3,5,6-tetrahydroimidazo-[1,2-c]-quinazoline

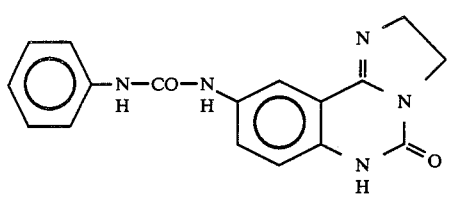

Melting point: >300° C.;
Yield: 78%.

EXAMPLE 51

9-N′-Benzoylureido-5-oxo-2,3,5,6-tetrahydroimidazo-[1,2-c]-quinazoline

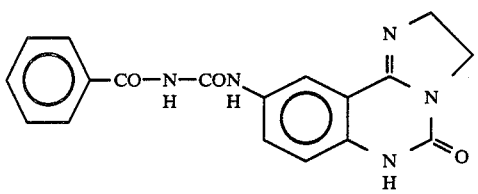

Melting point: >305° C.;
Yield: 99%.

The following compounds were obtained analogously to Example 48, using isothiocyanates as the starting materials:

EXAMPLE 52

9-N′-Methylthioureido-5-oxo-2,3,5,6-tetrahydroimidazo-[1,2-c]-quinazoline

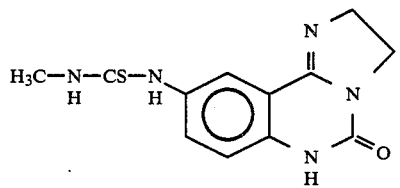

Melting point: >300° C.;
Yield: 69%.

EXAMPLE 53

9-N′-Phenylthioureido-5-oxo-2,3,5,6-tetrahydroimidazo-[1,2-c]-quinazoline

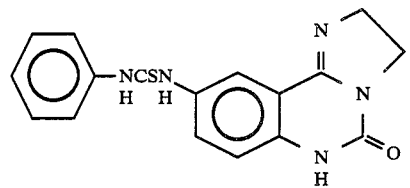

Melting point: >300° C.;
Yield: 56%.

EXAMPLE 54

9-(4-Morpholinylsulphonyl)-5-oxo-2,3,5,6-tetrahydroimidazo-[1,2-c]-quinazoline

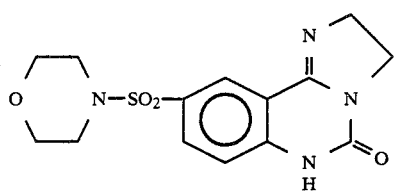

30 mmols of 5-oxo-2,3,5,6-tetrahydroimidazo-[1,2-c]-quinazoline were added, whilst cooling with ice, to 20 ml of chlorosulphonic acid, and the mixture was stirred for 3 hours at 50° to 60° C. After this solution had been cooled, it was carefully added dropwise to 80 ml of cooled morpholine, and the mixture was thereafter diluted with 150 ml of water. The residue was filtered off under suction, washed with water and boiled up with alcohol.

Melting point: >260° C.;
Yield: 27%.

EXAMPLE 55

9-Aminosulphonyl-5-oxo-2,3,5,6-tetrahydroimidazo-[1,2-c]-quinazoline

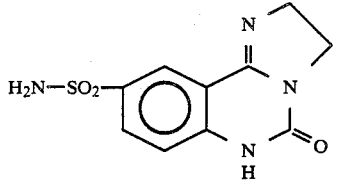

Melting point: >300° C.;
Yield: 23%.

(Preparation analogously to Example 54 by dropwise addition to concentrated NH$_3$).

EXAMPLE 56

9-(1-Piperazinylsulphonyl)-5-oxo-2,3,5,6-tetrahydroimidazo-[1,2-c]-quinazoline

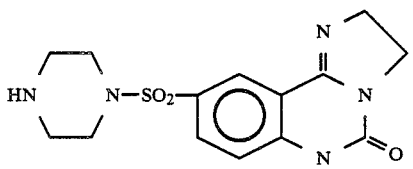

Melting point: >260° C.;
Yield: 18%.

(Preparation analogously to Example 54 by dropwise addition to piperazine).

EXAMPLE 57

9-Hydroxysulphonyl-5-oxo-2,3,5,6-tetrahydroimidazo-[1,2-c]-quinazoline

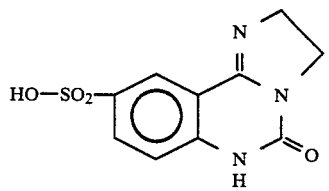

Melting point: >300° C.
(Preparation analogously to Example 54 by dropwise addition to water).

EXAMPLE 58

5-Oxo-2-methyl-2,3,5,6-tetrahydroimidazo-[1,2-c]-quinazoline

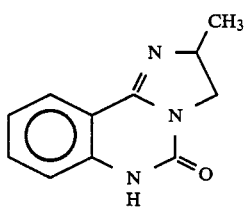

Preparation analogously to Example 1 by reaction with 1,2-diaminopropane instead of ethylenediamine.
Melting point: 255°–258° C.;
Yield: 20%.

EXAMPLE 59

5-Oxo-(2- and 3-phenyl)-2,3,5,6-tetrahydroimidazo-[1,2-c]-quinazoline hydrochloride

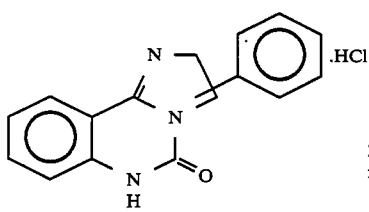

2:3 isomer mixture

Analogously to Example 1 by reaction with 2 equivalents of phenyl-1,2-diaminoethane.
After heating to 200° C. in tetralin and stripping off the tetralin in vacuo, the residue was dissolved in pyridine, and one equivalent of phenylchloroformate was added to the solution at room temperature.
After the mixture had been stirred overnight, water was added to it, it was concentrated in a rotary evaporator, and was heated together with tetralin to 220° C. for 1 hour. After the tetralin had been stripped off in vacuo, ethanol was added and the mixture was crystallised overnight.
Melting point: 246°–248° C.;
Yield: 10%.

EXAMPLE 60

6-Oxo-2,3,4,5,6,7-hexahydropyrimido[1,2-c]-quinazoline

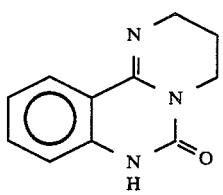

Preparation analogously to Example 1 using 1,3-diaminopropane instead of ethylenediamine.
Melting point: 248°–250° C. (from isopropanol);
Yield: 35%.

EXAMPLE 61

9-Benzenesulphonylamino-5-oxo-2,3,5,6-tetrahydroimidazo-[1,2-c]-quinazoline

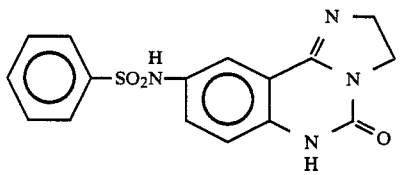

7.1 g of benzenesulphonic acid chloride were added to 4.04 g of 9-amino-5-oxo-2,3,5,6-tetrahydroimidazo-[1,2-c]-quinazoline in 50 ml of absolute pyridine, whilst cooling with ice. The cooling was removed and the mixture was stirred for 2 hours at room temperature. A large quantity of $H_2O$ was then added to the reaction mixture, and the precipitated crystals were filtered off under suction. The crystals were dissolved in aqueous $NH_3$ and the solution was clarified using active charcoal and neutralised using hydrochloric acid.
The precipitated crystals were filtered off under suction, washed with ethanol and ether, and dried.
Melting point: >300° C.;
Yield: 4.4 g (64%).
The following compounds were prepared analogously to Example 61:

EXAMPLE 62

9-o-Toluenesulphonylamino-5-oxo-2,3,5,6-tetrahydroimidazo-[1,2-c]-quinazoline

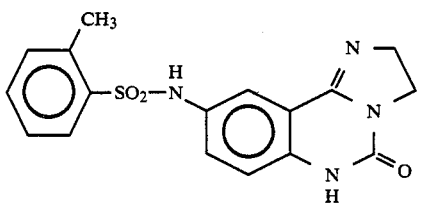

Melting point: >300° C.;
Yield: 72%.

EXAMPLE 63

9-p-Nitrobenzenesulphonylamino-5-oxo-2,3,5,6-tetrahydroimidazo[1,2-c]-quinazoline

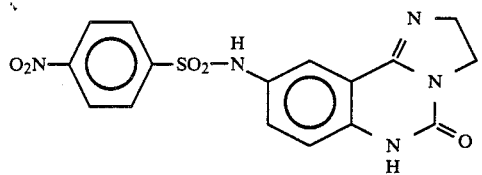

Melting point: >300° C.;
Yield: 36%.

EXAMPLE 64

9-Methanesulphonylamino-5-oxo-2,3,5,6-tetrahydroimidazo-[1,2-c]-quinazoline

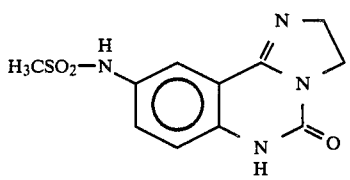

Melting point: >300° C.;
Yield: 59%.

EXAMPLE 65

9-Benzoylamino-5-oxo-2,3,5,6-tetrahydroimidazo-[1,2-c]-quinazoline

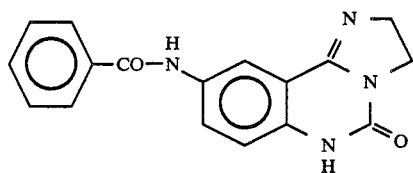

Melting point: >305° C. (from dimethylformamide);
Yield: 58%.

The compound was prepared analogously to Example 37.

EXAMPLE 66

9-Nitro-5-oxo-(2- or 3-methyl)-2,3,5,6-tetrahydroimidazo-[1,2-c]-quinazoline

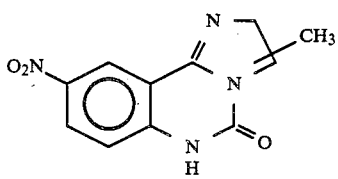

Yield: 52%;
Melting point: 265°-8°.

Preparation analogously to Example 31 by nitration of 5-oxo-(2- or 3-methyl)-2,3,5,6-tetrahydroimidazo-[1,2-c]-quinazoline.

EXAMPLE 67

9-Trifluoromethyl-5-oxo-(2- or 3-methyl)-2,3,5,6-tetrahydroimidazo-[1,2-c]-quinazoline

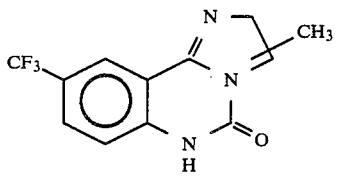

Yield: 5%;
Melting point; 270°-3° C.
Preparation analogously to Example 1.

EXAMPLE 68

9-Trifluoromethyl-5-oxo-(3- or 2-methyl)-2,3,5,6-tetrahydroimidazo-[1,2-c]-quinazoline

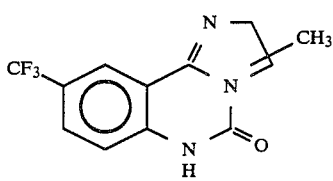

Yield: 3%;
Melting point: 190°-5° C.
Isolation from the mother liquor of Example 67 by chromatography using methanol.

EXAMPLE 69

9-Amino-5-oxo-(2- or 3-methyl)-2,3,5,6-tetrahydroimidazo-[1,2-c]-quinazoline

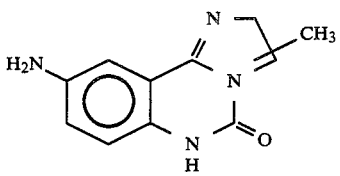

Yield: 40%;
Melting point: 260° C.
Preparation analogously to Example 33.

EXAMPLE 70

9-(4-Morpholinylsulphonyl)-5-oxo-(2- or 3-methyl)-2,3,5,6-tetrahydroimidazo-[1,2-c]-quinazoline

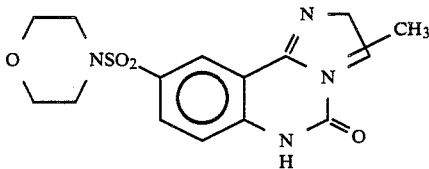

Yield: 33%;
Melting point: 260° C.

Preparation analogously to Example 54.

EXAMPLE 71

9-Isovaleroylamino-5-oxo-(2- or 3-methyl)-2,3,5,6-tetrahyroimidazo-[1,2-c]-quinazoline

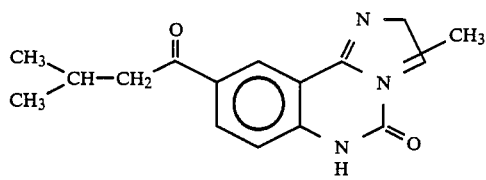

Yield: 27%;

Melting point: 260° C.

Preparation analogously to Example 37.

EXAMPLE 72

9-(2-Hydroxyethyl)-aminosulphonyl-5-oxo-(2- or 3-methyl)-2,3,5,6-tetrahydroimidazo-[1,2-c]-quinazoline

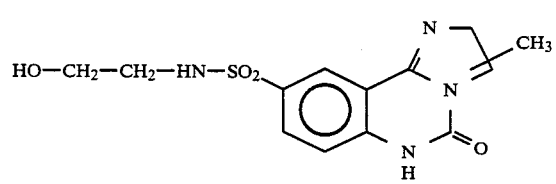

Yield: 5%;

Melting point: 241°–50° C.

Preparation analogously to Example 54 by dropwise addition to 2-aminoethanol.

EXAMPLE 73

9-Trifluoromethyl-5-oxo-(2- or 3-methyl)-6-allyl-2,3,5,6-tetrahydroimidazo-[1,2-c]-quinazoline

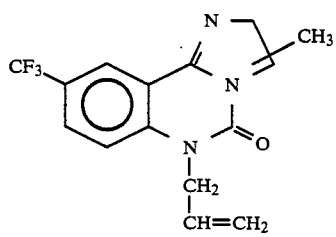

Yield: 68%;

Melting point; 94°–96° C.

Preparation analogously to Example 29.

EXAMPLE 74

10-Trifluoromethoxy-6-oxo-3,3-dimethyl-2,3,4,5,6,7-hexahydropyrimido-[1,2-c]-quinazoline

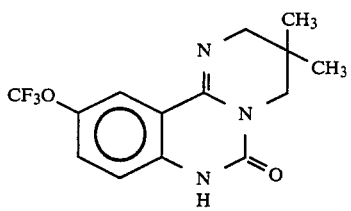

Yield: 11%;

Melting point: 210°–215° C.

Preparation analogously to Example 1 using 1,3-diamino-2,2-dimethylpropane.

EXAMPLE 75

10-Trifluoromethyl-6-oxo-3,3-dimethyl-2,3,4,5,6,7-hexahydropyrimido-[1,2-c]-quinazoline

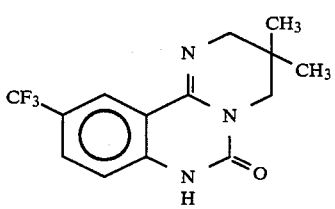

Yield: 11%;

Melting point: >260° C.

Preparation analogously to Example 1 using 1,3-diamino-2,2-dimethylpropane.

EXAMPLE 76

9-Trifluoromethoxy-5-oxo-(3- or 2-methyl)-2,3,5,6-tetrahydroimidazo-[1,2-c]-quinazoline

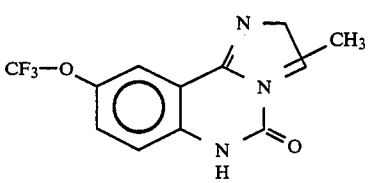

Yield: 10%;

Melting point: 240°–2° C.

Preparation analogously to Example 1 and precipitation with acetone.

EXAMPLE 77

9-Trifluoromethoxy-5-oxo-(2- or 3-methyl)-2,3,5,6-tetrahydroimidazo-[1,2-c]-quinazoline

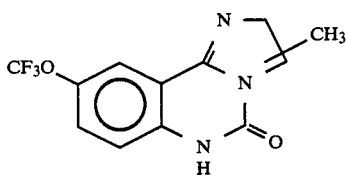

Yield: 15%;
Melting point: 205°–210° C.
Isolation from the mother liquor of Example 76 by chromatography using ethyl acetate.

EXAMPLE 78

7,9-Dibromo-5-oxo-(2- and 3-methyl)-2,3,5,6-tetrahydroimidazo-[1,2-c]-quinazoline

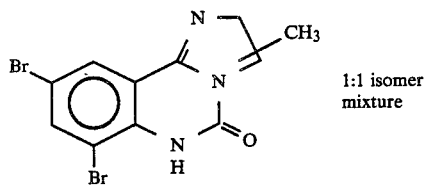

1:1 isomer mixture

Yield: 30%;
Melting point: 220°–5° C.
Preparation analogously to Example 1.

EXAMPLE 79

7,9-Dichloro-5-oxo-(2- and 3-methyl)-2,3,5,6-tetrahydroimidazo-[1,2-c]-quinazoline

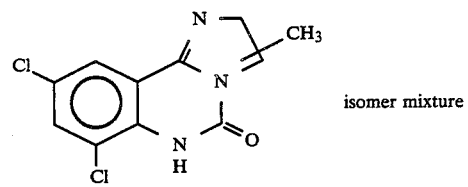

isomer mixture

Yield: 21%;
Melting point: 215°–9° C.
Preparation analogously to Example 1.

EXAMPLE 80

6-Oxo-3-hydroxy-2,3,4,5,6,7-hexahydropyrimido-[1,2-c]-quinazoline

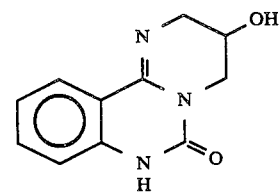

Yield: 25%;
Melting point: >260° C.
Preparation analogously to Example 1 using 1,3-diaminopropan-2-ol instead of ethylenediamine.

EXAMPLE 81

10-Nitro-6-oxo-2,3,4,5,6,7-hexahydropyrimido-[1,2-c]-quinazoline

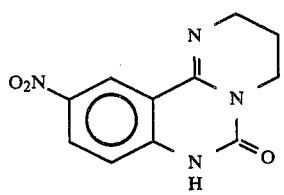

Preparation analogously to Example 1 by nitration of 6-oxo-2,3,4,5,6,7-hexahydropyrimido-[1,2-c]-quinazoline.
Melting point: >300° C.;
Yield: 54.8%.

EXAMPLE 82

10-Amino-6-oxo-2,3,4,5,6,7-hexahydropyrimido-[1,2-c]-quinazoline

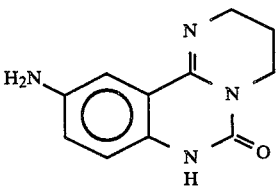

Preparation analogously to Example 33 by reduction of 10-nitro-6-oxo-2,3,4,5,6,7-hexahydropyrimido-[1,2-c]-quinazoline using sodium dithionite.
Melting point: 280° C. (decomposition);
Yield: 50%.

EXAMPLE 83

10-Nitro-6-oxo-7-allyl-2,3,4,5,6,7-hexahydropyrimido-[1,2-c]-quinazoline

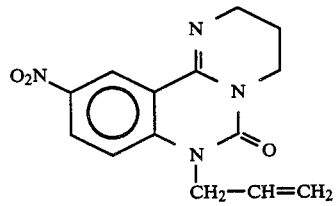

Preparation analogously to Example 29 from 10-nitro-6-oxo-2,3,4,5,6,7-hexahydropyrimido-[1,2-c]-quinazoline and allyl bromide.
Melting point: 242°–245° C.,
Yield: 45.5%.

EXAMPLE 84

9-(3-Methylbenzoylamino)-5-oxo-2,3,5,6-tetrahydroimidazo-[1,2-c]-quinazoline

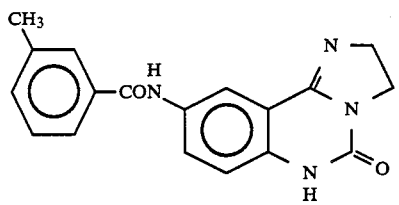

Preparation analogously to Example 37.
Melting point: >300° C.;
Yield: 39%.

EXAMPLE 85

9-(4-Chlorobenzoylamino)-5-oxo-2,3,5,6-tetrahydroimidazo-[1,2-c]-quinazoline

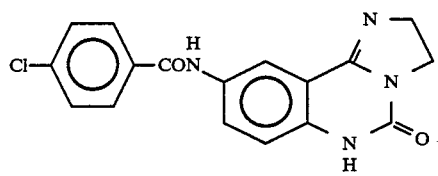

Preparation analogously to Example 37.
Melting point: >300° C.;
Yield: 38%.

EXAMPLE 86

9-(2,5-Dichlorobenzoylamino)-5-oxo-2,3,5,6-tetrahydroimidazo-[1,2-c]-quinazoline

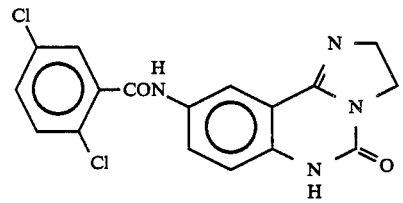

Preparation analogously to Example 37.
Melting point: >300° C.;
Yield: 27%.

EXAMPLE 87

9-(4-Chloro-3-nitrobenzoylamino)-5-oxo-2,3,5,6-tetrahydroimidazo-[1,2-c]-quinazoline Preparation analogously to Example 37.
Melting point: >300° C.;
Yield: 70%.

EXAMPLE 88

10-Trifluoromethyl-6-oxo-2,3,4,5,6,7-hexahydropyrimido-[1,2-c]-quinazoline

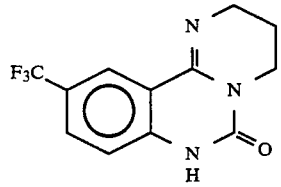

Preparation analogously to Example 1 from 2-amino-5-trifluoromethylbenzoic acid and 1,3-diaminopropane.
Melting point: 259°-260° C.;
Yield: 35%.

EXAMPLE 89

10-Trifluoromethyl-6-oxo-7-allyl-2,3,4,5,6,7-hexahydropyrimido-[1,2-c]-quinazoline

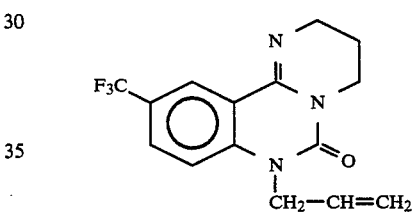

Preparation analogously to Example 29 from 10-trifluoromethyl-6-oxo-2,3,4,5,6,7-hexahydropyrimido-[1,2-c]-quinazoline and allyl bromide.
Melting point: 122°-125° C.;
Yield: 30%.

EXAMPLE 90

10-Trifluoromethoxy-6-oxo-2,3,4,5,6,7-hexahydropyrimido-[1,2-c]-quinazoline

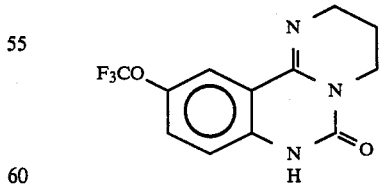

Preparation analogously to Example 1 from 2-amino-5-trifluoromethoxybenzoic acid and 1,3-diaminoprene.
Melting point: 257°-260° C.;
Yield: 28%.

EXAMPLE 91

10-Trifluoromethoxy-7-allyl-6-oxo-2,3,4,5,6,7-hexahydropyrimido-[1,2-c]-quinazoline

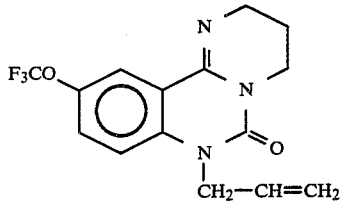

Preparation analogously to Example 29 from 10-trifluoromethoxy-6-oxo-2,3,4,5,6,7-hexahydropyrimido-[1,2-c]-quinazoline and allyl bromide.
Melting point: 103°–105° C.;
Yield: 37%.

EXAMPLE 92

5-Oxo-(2,2- or 3,3)-dimethyl-2,3,5,6-tetrahydroimidazo-[1,2-c]-quinazoline

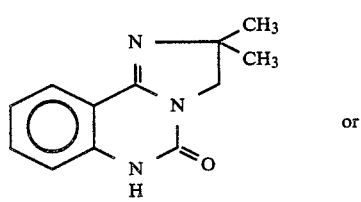 or 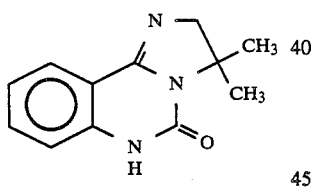

Structure not determined.
Preparation analogously to Example 1 from anthranilic acid and 1,2-diamino-2-methylpropane.
Melting point: 253°–255° C.,
Yield: 32%.

EXAMPLE 93

9-Trifluoromethyl-5-oxo-(2,2- or 3,3)-dimethyl-2,3,5,6-tetrahydroimidazo-[1,2-c]-quinazoline

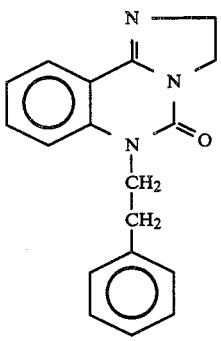 or 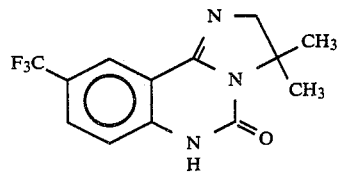

Structure not determined.
Preparation analogously to Example 1 from 2-amino-5-trifluoromethylbenzoic acid and 1,2-diamino-2-methylpropane.
Melting point: 228°–232° C.;
Yield: 25%.

EXAMPLE 94

9-Phenylacetamido-5-oxo-2,3,5,6-tetrahydroimidazo-[1,2-c]-quinazoline

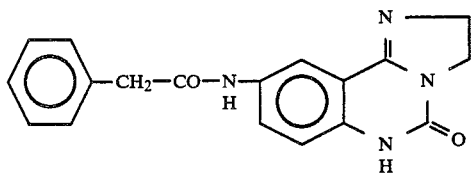

Preparation analogously to Example 37.
Melting point: >300° C.;
Yield: 78%.

EXAMPLE 95

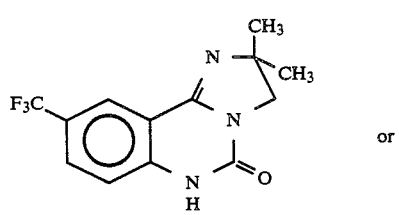

Preparation analogously to Example 29 from 5-oxo-2,3,5,6-tetrahydroimidazo-[1,2-c]-quinazoline and 2-phenylethyl bromide.
Melting point: 133°–135° C.;
Yield: 48.1%.

EXAMPLE 96

9-Acetamido-5-oxo-6-methyl-2,3,5,6-tetrahydroimidazo-[1,2-c]-quinazoline

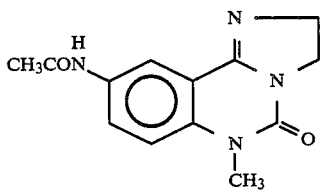

Preparation analogously to Example 37 from 9-amino-5-oxo-2,3,5,6-tetrahydroimidazo-[1,2-c]-quinazoline and acetic anhydride.
Melting point: 283°–286° C.;
Yield: 70%.

EXAMPLE 97

9-Propionylamino-5-oxo-6-methyl-2,3,5,6-tetrahydroimidazo-[1,2-c]-quinazoline

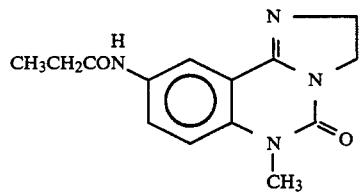

Preparation analogously to Example 37 from 9-amino-5-oxo-2,3,5,6-tetrahydroimidazo-[1,2-c]-quinazoline and propionic acid chloride.
Melting point: 215°–218° C.;
Yield: 59%.

EXAMPLE 98

9-Isovaleroylamino-5-oxo-6-methyl-2,3,5,6-tetrahydroimidazo-[1,2-c]-quinazoline

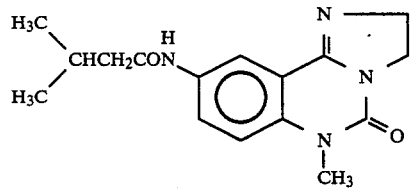

Preparation analogously to Example 37 from 9-amino-5-oxo-2,3,5,6-tetrahydroimidazo-[1,2-c]-quinazoline and isovaleric acid chloride.
Melting point: 137°–140° C.;
Yield: 60%.

EXAMPLE 99

9-Acetoamido-5-oxo-6-benzyl-2,3,5,6-tetrahydroimidazo-[1,2-c]-quinazoline

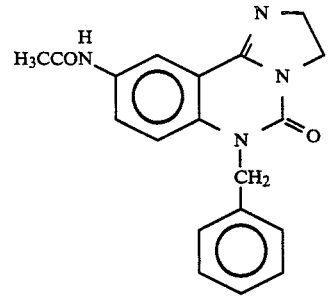

Preparation analogously to Example 37 from 9-amino-5-oxo-6-benzyl-2,3,5,6-tetrahydroimidazo-[1,2-c]-quinazoline and acetic anhydride.
Melting point: 270°–272° C.;
Yield: 84%.

EXAMPLE 100

9-Propionylamino-5-oxo-6-benzyl-2,3,5,6-tetrahydroimidazo-[1,2-c]-quinazoline

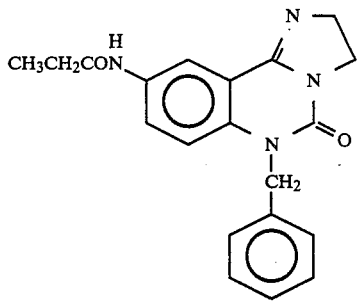

Preparation analogously to Example 37 from 9-amino-5-oxo-6-benzyl-2,3,5,6-tetrahydroimidazo-[1,2-c]-quinazoline and propionic acid chloride.
Melting point: 125°–129° C.;
Yield: 75%.

EXAMPLE 101

9-Isovaleroylamino-5-oxo-6-benzyl-2,3,5,6-tetrahydroimidazo-[1,2-c]-quinazoline

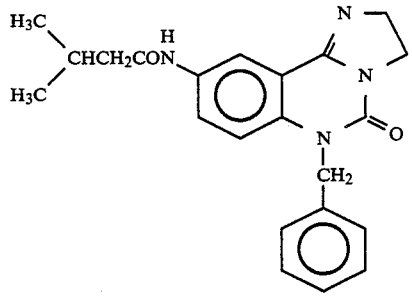

Preparation analogously to Example 37 from 9-amino-5-oxo-6-benzyl-2,3,5,6-tetrahydroimidazo-[1,2-c]-quinazoline and isovaleric acid chloride.
Melting point: 173°–178° C.;
Yield: 95%.

EXAMPLE 102

6-(3-Trifluoromethylphenyl)-2,3-dihydro-imidazo-[1,2-c]-quinazolin-5-one (a) 2-(2-(3-Trifluoromethylphenylamino)-phenyl)-2-imidazoline

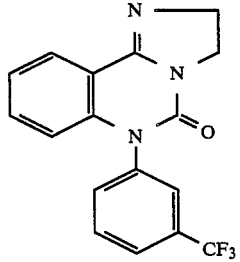

A mixture of 20.2 g (60 mmol) of 2-(3-trifluoromethylphenylamino)-benzoic acid n-butyl ester and 28.2 ml (0.42 mol) of ethylenediamine were heated in an autoclave for 21 hours to 200° C. After the reaction mixture had been cooled, it was diluted with water and extracted with dichloromethane. The extract was dried over Na$_2$SO$_4$, concentrated by evaporation and subjected to chromatography over silica gel (running agent ethyl acetate/methanol 7:3).

Yield: 30% of theory;

Melting point: 95°–96° C. (foam).

(b) 6-(3-Trifluoromethylphenyl)-2,3-dihydro-imidazo-[1,2-c]-quinazolin-5-one 3.26 g (75 mmol) of sodium hydride were added to a solution of 10.4 g (34 mmol) of 2-(2-(3-trifluoromethylphenylamino)-phenyl)-2-imidazoline in 100 ml of absolute tetrahydrofuran, and the mixture was warmed to 50° to 60° C. until evolution of hydrogen had ceased (5 to 6 hours). After the reaction mixture had cooled to room temperature, 16 ml (0.166 mol) of ethyl chloroformate were added dropwise to it and it was boiled under reflux for one hour. The mixture was allowed to cool, the pH was adjusted to 4–5 with glacial acetic acid, and the mixture was diluted with water and extracted with dichloromethane. The organic phase was dried over Na$_2$SO$_4$ and concentrated, and the residue was subjected to chromatography over silica gel (running agent ethyl acetate/methanol 7:3), and the residue from the evaporation of the product-containing fractions was thoroughly stirred with ether/petroleum ether 1:3.

Yield: 24% of theory;

Melting point 211°–213° C.

EXAMPLE 103

6-(2-Fluoro-4-nitrophenyl)-2,3-dihydro-imidazo-[1,2-c]-quinazolin-5-one

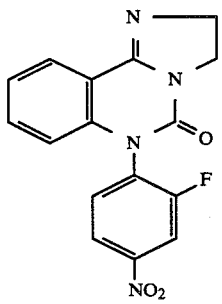

(a) 2-(2-Fluoro-4-nitrophenylamino)-benzonitrile 21.8 g (0.5 mol) of sodium hydride were added in portions to a solution of 59 g (0.5 mol) of 2-aminobenzonitrile and 53.2 ml (0.5 mol) of 3-fluoronitrobenzene in absolute dimethylformamide, whereby the reaction mixture warmed up to 80° C., with a change in colour from dark green to dark red. After the mixture had been cooled to room temperature, it was diluted with water and acidified with 2N hydrochloric acid, and the precipitate formed was filtered off. The precipitate was purified by chromatography over silica gel using dichloromethane, and the residue from evaporation of the product-containing fractions was thoroughly stirred with ether/petroleum ether 1:2.

Yield 27% of theory;

Melting point: 185°–186° C.

(b) 2-(2-(2-Fluoro-4-nitrophenylamino)-phenyl)-2-imidazoline

A mixture of 8.5 g (33 mmol) of 2-(2-fluoro-4-nitrophenylamino)-benzonitrile and 16.7 ml (249 mmol) of ethylenediamine was heated in an autoclave to 180° for 1 hour, and the reaction mixture was then worked up as described in Example (1a). After crystallisation from dichloromethane and ether/petroleum ether, the reaction product was obtained in a 60% yield.

Melting point 155°–156° C.

(c) 6-(2-Fluoro-4-nitrophenyl)-2,3-dihydro-imidazo-[1,2-c]-quinazolin-5-one 1.1 g (25 mmol) of sodium hydride were added to a solution of 3.47 g (11.6 mmol) of 2-(2-(2-fluoro-4-nitrophenylamino)-phenyl)-2-imidazoline in 60 ml of absolute tetrahydrofuran, and the mixture was warmed to 50° C. until the evolution of hydrogen had ended. After the reaction mixture had been cooled to room temperature, 5.8 ml (60 mmol) of ethyl chloroformate in 10 ml of absolute tetrahydrofuran were added dropwise to it and it was warmed to 50° C. for 90 minutes. The reaction mixture was allowed to cool to room temperature, acidified with glacial acetic acid, diluted with water and extracted with dichloromethane. The organic phase was concentrated by evaporation, water was added to the residue, and the solution was adjusted to a pH of 1–2 with hydrochloric acid and was extracted with dichloromethane. The precipitate which occurred on addition of KHCO$_3$ solution to the aqueous phase was filtered off under suction, washed with water and dried.

Yield: 27% of theory;

Melting point: 223°–224° C.

EXAMPLE 104

6-(3-Nitrophenyl)-2.3-dihydro-imidazo[1.2-c]quinazolin-5-one

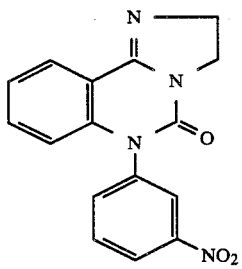

(a) 2-(3-Nitrophenylamino)benzonitrile 3,85 g (15 mMol) of 2-(3-Nitrophenylamino)benzoic acid amide in 30 ml (0,325 Mol) phosphorooxychloride were treated with 4,32 ml (31 mMol) triethylamine which is added dropwise, whereby the reaction mixture warms up. After thirty minutes the excess of phosphorooxychloride is distilled off, the residue is treated with water and the solid product is filtered off.

Yield: 3,2 g (89,3% of theory);

Melting point: 165°–166° C.

(b) 2-(2-(3-Nitrophenylamino)phenyl)imdiazolin-2

A mixture of 2,39 g (10 mMol) 2-(3-Nitrophenylamino)benzonitrile and of 4,7 ml (70 mMol) ethylendiamine is heated in an autoclave to 180° C. for 1½ hour, and the reaction mixture is then worked up as described in example (104a).

Yield: 1 g (35,5% of theory);

Melting point: 113°–115° C.

(c) 6-(3-Nitrophenyl)-2.3-dihydro-imidazo[1.2-c]quinazolin-5-one

A suspension of 1,21 g (4,3 mMol) of 2-(2-(3-Nitrophenylamino)phenyl)imidazoline-2 in 10 ml toluene is treated with 2,4 ml (17 mMol) of triethylamine and then with 10 ml of a solution of phosgen in toluene (10%).

The mixture warms up and is solved by adding 85 ml dichloromethane and afterwards heated under reflux for one hour. After cooling the reaction mixture is washed with KHCO$_3$-solution and water, the organic phase is dried over Na$_2$SO$_4$ and the organic solution is distilled off. After chromatography on silica-gel (acetoacetic acid ethylester/methanol 7:3) the fractions containing the product are combined the solvent is distilled off and the residue is taken up in 2N hydrochloric acid. The solution is treated with active coal and then adjusted to a pH of 9–10 with a solution of 2N NaOH. The precipitate which occured is filtered off, washed with water and dried.

Yield: 350 mg (26,3% of theory);
Melting point: 270°–271° C.

What is claimed is:

1. A pharmaceutical composition containing as an active ingredient an amount effective for treating cardiac insufficiencies, of a compound of the formula

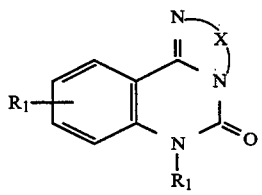

in which
- X represents a bridge member having 2 or 3 carbon atoms, which is optionally substituted by 1 or 2 C$_1$–C$_4$ alkyl radicals
- R$_1$ represents a hydrogen atom or a C$_1$–C$_{18}$ alkyl or alkenyl radical, the alkenyl radical containing 1 or 2 double bonds, a phenyl or a benzyl radical, both optionally being substituted by a CF$_3$ group, a fluorine or a nitro group,
- R$_4$ represents
  - a hydrogen atom,
  - a nitro group,
  - an acylamino group containing an acyl radical, the acyl radical being derived from a C$_1$–C$_{12}$ aliphatic carboxylic acid or a phenyl carboxylic acid, which is optionally substituted in the phenyl radical by OH, halogen C$_1$–C$_4$ alkyl, C$_1$–C$_4$ alkoxy, nitro or amino, a sulfonylamino group containing a sulfonyl radical, the sulfonyl radical being derived from an C$_1$–C$_6$ aliphatic sulfonic acid or a phenyl sulfonic acid, the phenyl radical of which can be substituted by NO$_2$, amino, acetamido, C$_1$–C$_4$ alkyl, C$_1$–C$_4$ alkoxy, halogen or CF$_3$, an aminosulfonic group of (1) ammonium, (2) a C$_1$–C$_{12}$ primary or secondary amine, (3) a heterocyclic amine selected from the group consisting of piperidine, pyrrolidine, morpholine and piperazine or (4) aniline or an aniline which is optionally substituted by halogen, C$_1$–C$_4$ alkyl or C$_1$–C$_4$ alkoxy, optionally being substituted by halogen, C$_1$–C$_4$—alkyl or C$_1$–C$_4$—alkoxy,
  - trifluoromethyl or
  - trifluoromethoxy.

2. A pharmaceutical composition containing as an active ingredient an amount effective for treating cardiac insufficiencies, of a compound of the formula

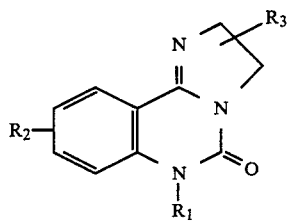

in which
- R$_1$ is hydrogen, alkyl, alkenyl, or alkynyl, each with up to 18 atoms of carbon, aralkyl, C$_1$–C$_4$—alkyl—N—(C$_1$–C$_4$—alkyl)$_2$, C$_1$–C$_4$—alkyl-phenyl(Cl)$_x$, wherein x is 1 or 2, phenyl optionally substituted with 1 to 3 identical or different substituents selected from NO$_2$, halogen, or CF$_3$,
- R$_2$ is C$_1$–C$_6$—alkyl and alkenyl; phenyl; C$_1$–C$_6$—alkoxy; phenoxy; C$_1$–C$_6$—alkylthio; phenylthio; C$_1$–C$_6$—alkylsulfonyl; phenylsulfonyl; acetyl; benzoyl; trifluoromethyl; trifluoromethoxy; trifluoromethylthio; hydroxymethyl, aminomethyl, C$_1$–C$_6$—alkylcarbonyloxymethyl, C$_1$–C$_4$—alkylcarbonylaminomethyl, phenethyl; C$_1$–C$_4$—alkylcarbonyloxy; C$_1$–C$_4$—mono- and dialkylamino; acylamino, wherein the acyl radical is derived from aliphatic carboxylic acid with 1 to 12 carbon atoms; C$_1$–C$_5$—alkoxycarbonylamino; a urea radical, wherein the second nitrogen atom is substituted with C$_1$–C$_{12}$—alkyl, or phenyl, or sulfonylamino, wherein the sulfonyl radical is derived from aliphatic sulfonic acids with 1 to 6 carbon atoms or from phenylsulfonic acids with a phenyl radical that can be substituted with NO$_2$, amino, acetamido, C$_1$–C$_4$—alkyl, C$_1$–C$_4$—alkoxy, halogen, or CF$_3$; or carbonamido of ammonia, of C$_1$–C$_{12}$ aliphatic primary or secondary amines, of heterocyclic amines selected from the group consisting of piperidine, pyrrolidine, morpholine, and piperazine, of aniline or an aniline, which is substituted with halogen C$_1$–C$_4$—alkyl, or C$_1$–C$_4$—alkoxy; a sulfonic-acid group, a sulfonamido of NH$_3$, C$_1$–C$_{12}$ primary or secondary amines, of piperidine, piperazine, or morpholine, F, Cl, or Br, and
- R$_3$ represents hydrogen, C$_1$–C$_4$—alkyl, phenyl, or benzyl as well as their pharmaceutically compatible salts with inorganic or organic acids.

3. A compound of the formula

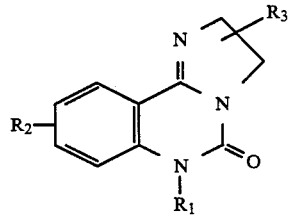

in which
- R$_1$ is hydrogen, alkyl, alkenyl, or alkynyl, each with up to 18 atoms of carbon, aralkyl, C$_1$–C$_4$—alkyl—N—(C$_1$–C$_4$—alkyl)$_2$, C$_1$–C$_4$—alkyl-phenyl(cl)$_x$, wherein x is 1 or 2, phenyl optionally substituted with 1 to 3 identical or different substituents selected from NO$_2$, halogen, or CF$_3$, $R_2$ is $C_1$-$C_6$—alkyl and alkenyl; phenyl; $C_1$-$C_6$—alkoxy; phenoxy; $C_1$-$C_6$—alkylthio, phenylthio; $C_1$-$C_6$—alkylsulfonyl; phenylsulfonyl; acetyl; benzoyl; trifluoromethyl; trifluoromethoxy; trifluoromethylthio; hydroxymethyl, aminomethyl, $C_1$-$C_6$—alkylcarbonyloxymethyl, $C_1$-$C_4$—alkylcarbonylaminomethyl, phenethyl, $C_1$-$C_4$—alkylcarbonyloxy; $C_1$-$C_4$—mono- and dialkylamino; acylamino, wherein the acyl radical is derived from aliphatic carboxylic acid with 1 to 12 carbon atoms; $C_1$-$C_4$—alkoxycarbonylamino; a urea radical, wherein the second nitrogen atom is substituted with $C_1$-$C_{12}$—alkyl, or phenyl, or sulfonylamino, wherein the sulfonyl radical is derived from aliphatic sulfonic acids with 1 to 6 carton atoms or from phenylsulfonic acids with a phenyl radical that can be substituted with $NO_2$, amino, acetamido, $C_1$-$C_4$—alkyl, $C_1$-$C_4$—alkoxy, halogen, or $CF_3$; or carbonamido of ammonia, of $C_1$-$C_{12}$ aliphatic primary or secondary amines, of heterocyclic amines selected from the group consisting of piperidine, pyrrolidine, morpholine, piperazine, of aromatic amines, which are unsubstituted or substituted with halogen $C_1$-$C_4$—alkyl, or $C_1$-$C_4$—alkoxy; a sulfonic-acid group, a sulfonamido of $NH_3$, $C_1$-$C_{12}$ primary or secondary amines, of piperidine, piperazine, or morpholine, F, Cl, or Br, and $R_3$ represents hydrogen, $C_1$-$C_4$—alkyl, phenyl, or benzyl as well as their pharmaceutically compatible salts with inorganic or organic acids.

4. A composition according to claim 1 in which the active ingredient is 9-Trifluoromethyl-5-oxo-2,3,5,6-tetrahydroimidazo-[1,2-c]-quinazoline.

5. A composition according to claim 1 in which the active ingredient is 9-Isovaleroylamino-5-oxo-2,3,5,6-tetrahydroimidazo-[1,2-c]-quinazoline.

6. A composition according to claim 1 in which the active ingredient is 9-(4-Morpholinylsulphonyl)-5-oxo-2,3,5,6-tetrahydroimidazo-[1,2-c]-quinazoline.

7. A composition according to claim 1 in which the active ingredient is 9-Trifluoromethyl-5-oxo-(3- or 2-methyl)-2,3,5,6-tetrahydroimidazo-[1,2-c]-quinazoline.

8. A composition according to claim 1 in which the active ingredient is 10-Nitro-6-oxo-7-allyl-2,3,4,5,6,7-hexahydropyrimido-[1,2-c]-quinazoline.

9. A pharmaceutical composition of claims 1 in the form of a sterile or physiologically isotonic aqueous solution.

10. A composition according to claims 1, containing from 0.5 to 95% of the said active ingredient, by weight.

11. A medicament in dosage unit form comprising an amount effective for treating cardiac insufficiencies, of a compound as defined in claims 1 either alone or in admixture with a diluent.

12. A medicament of claim 1 in the form of tablets, pills, dragees, capsules, ampoules, or suppositories comprising a compound as defined in claim 1 either alone or in admixture with a diluent.

13. A method of combating circulatory illnesses in warm-blooded animals which comprises administering to the animals a compound effective for treating cardiac insufficiencies as defined in claim 1 either alone or in admixture with a diluent or in the form of a medicament.

14. A method according to claim 13 in which the active compound is administered orally in an amount of 0.1 to 100 mg per kg body weight per day.

15. A method according to claim 14 in which the active compound is administered orally in an amount of 1.0 to 50 mg/kg of body weight per day.

16. A pharmaceutical composition of claim 1 containing, as an active ingredient, an amount of active compound effective for treating congestive heart failure.

17. A method of treating congestive heart failure in warm-blooded animals which comprises administering to the animals a compound effective for treating congestive heart failure as defined in claim 1 either alone or in admixture with a diluent or in the form of a medicament.

18. A compound of claim 3 which is 9-Trifluoromethyl-5-oxo-2,3,5,6-tetrahydroimidazo-[1,2-c]-quinazoline.

19. A compound of claim 3 which is 9-Isovaleroylamino-5-oxo-2,3,5,6-tetrahydroimidazo-[1,2-c]-quinazoline.

20. A compound of claim 3 which is 9-(4-Morpholinysulphonyl)-5-oxo-2,3,5,6,-tetrahydroimidazo-[1,2-c]-quinazoline.

21. A compound of claim 3 which is 9-Trifluoromethyl-5-oxo(3- or 2-methyl)-2,3,5,6,-tetrahydroimidazo-[1,2-c]-quinazoline.

* * * * *

UNITED STATES PATENT AND TRADEMARK OFFICE
CERTIFICATE OF CORRECTION

PATENT NO. : 4,585,772
DATED : April 29, 1986
INVENTOR(S) : Bodo Junge, et al.

It is certified that error appears in the above-identified patent and that said Letters Patent is hereby corrected as shown below:

| | |
|---|---|
| Col. 3, line 50 | Before "from" insert --selected-- |
| Col. 8, line 32 | Delete "reaction" and substitute --residue-- |
| Col. 8, line 52 | Delete "catalysts" and substitute --catalysis-- |
| Col. 10, line 8 | After "ingredient" insert --only-- |
| Col. 19, line 53 | Before "pyrido" insert -- - -- |
| Col. 20, line 4 | After "pyrido" insert -- - -- |
| Col. 36, line 20 | After "Example" delete "1" and substitute --31-- |
| Col. 48, line 8 | Before "1" delete "claims" and substitute --claim-- |

Signed and Sealed this

Fifth Day of August 1986

[SEAL]

Attest:

Attesting Officer

DONALD J. QUIGG

Commissioner of Patents and Trademarks